（12） United States Patent
Key

(10) Patent No.: US 9,274,009 B2
(45) Date of Patent: *Mar. 1, 2016

(54) APPARATUS AND METHOD FOR MEASUREMENT OF THE FILM COOLING EFFECT PRODUCED BY AIR COOLED GAS TURBINE COMPONENTS

(71) Applicant: Meyer Tool, Inc., Cincinnati, OH (US)

(72) Inventor: Douglas E. Key, Batavia, OH (US)

(73) Assignee: Meyer Tool, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/288,484

(22) Filed: May 28, 2014

(65) Prior Publication Data

US 2014/0330534 A1  Nov. 6, 2014

Related U.S. Application Data

(63) Continuation of application No. 12/948,088, filed on Nov. 17, 2010, now Pat. No. 8,768,646.

(60) Provisional application No. 61/261,837, filed on Nov. 17, 2009.

(51) Int. Cl.
| G01K 7/00 | (2006.01) |
| G06F 17/00 | (2006.01) |
| G06F 19/00 | (2011.01) |
| G01K 17/08 | (2006.01) |
| G01J 5/00 | (2006.01) |
| G01N 25/20 | (2006.01) |

(52) U.S. Cl.
CPC . *G01K 17/08* (2013.01); *G01J 5/00* (2013.01); *G01J 5/0088* (2013.01); *G01K 7/00* (2013.01); *G01N 25/20* (2013.01); *G01J 2005/0077* (2013.01); *G06F 17/00* (2013.01); *G06F 19/00* (2013.01)

(58) Field of Classification Search
None
See application file for complete search history.

(56) References Cited

U.S. PATENT DOCUMENTS

| 2,975,629 A | 3/1961 | Herbert |
| 3,142,983 A | 8/1964 | Dudley et al. |
| 4,902,139 A | 2/1990 | Adiutori |
| 7,388,204 B2 | 6/2008 | Key et al. |
| 7,671,338 B2 | 3/2010 | Key |
| 7,791,025 B2 | 9/2010 | Key |
| 8,244,488 B2 | 8/2012 | Allen et al. |
| 8,768,646 B2 | 7/2014 | Key |
| 2011/0125423 A1 | 5/2011 | Allen et al. |

Primary Examiner — Edward Cosimano
(74) Attorney, Agent, or Firm — Wood, Herron & Evans, LLP

(57) ABSTRACT

A method for measurement of a film cooling effect is disclosed. Film cooling is a technique developed to protect gas turbine engine components from the extremely high temperatures created during its operation. A controlled air pressure is ducted into the hollow interior of the component and the mass rate of air flowing through the plurality of film cooling features or openings is measured. A coolant is then injected into the hollow interior of the component and allowed to flow out of a film cooling feature onto the heated outer surface of the component. The resulting infrared signature is a measure of the relative cooling effect generated by the individual film cool feature. The film cooling effect for an individual feature is quantified as the proportion of mass rate of airflow contributed by its relative individual cooling effect. The area, location and shape of the cooling effect are further classified to determine the degree of conformance to its design intent.

20 Claims, 28 Drawing Sheets

APPARATUS AND METHOD FOR MEASUREMENT OF THE FILM COOLING EFFECT PRODUCED BY AIR COOLED GAS TURBINE COMPONENTS

CROSS REFERENCE TO RELATED APPLICATIONS

This application is a continuation of U.S. patent application Ser. No. 12/948,088 filed Nov. 17, 2010 entitled "Apparatus and Method for Measurement of the Film Cooling Effect Produced by Air Cooled Gas Turbine Components", now U.S. Pat. No. 8,768,646, which is incorporated by reference in its entirety. U.S. patent application Ser. No. 12/948,088 is based upon and claims priority U.S. Provisional Patent Application Ser. No. 61/261,837, filed Nov. 17, 2009, entitled "Apparatus and Method for Measurement of the Film Cooling Effect Produced by Air Cooled Gas Turbine Components", which is incorporated by reference in its entirety.

FIELD OF THE INVENTION

The present invention relates to the measurement of the film cooling effect generated by cooling features fabricated in gas turbine components. More particularly, the film cooling effect generated by features fabricated in gas turbine blades.

BACKGROUND OF INVENTION

Gas turbine engines have been used for decades for propulsion, power generation and other industrial applications. A gas turbine engine extracts energy from the flow of combustion gas. It has an upstream compressor coupled to a downstream turbine with a combustion chamber positioned between. Energy is added to the stream of compressed air in the combustor where fuel is mixed with the air and ignited. This combustion increases the temperature, velocity and volume of gas. The hot gas is diverted through a stationary nozzle that is then deflected onto turbine blades, spinning the turbine rotor and powering the compressor. Additional stages of vanes and blades are used to produce more work. Energy is extracted in the form of shaft power or thrust. The thermal efficiency and power output of these engines increases with increased turbine rotor inlet temperature, up to the hydrocarbon fuel stoichiometric limit of about 4,200 degrees Fahrenheit. With the melting temperature of the nickel based super alloys used to fabricate components for gas turbines at about 2,000 degrees Fahrenheit, it should be evident that cooling a gas turbine component is critical to its sustained operation. In the case of a gas turbine blade, combinations of thermal barrier coatings and sophisticated cooling techniques have been developed to maintain the blade's temperature at a safe operating point.

Referring to FIG. 1, as with other components in a gas turbine engine, a turbine blade (10) is formed as a hollow airfoil that is cooled both internally and externally. The coolant used for this purpose is extracted from the compressor, resulting in a reduction in the thermal efficiency for the engine. As such, the amount of coolant extracted is minimized by design and its mass becomes a major design characteristic for the turbine blade. Internal cooling is accomplished by injecting the coolant through an opening (7) in the bottom of the blade and allowed to flow through a series of serpentine passages inside the blade, where heat is extracted from the inner airfoil surface. In addition, jet impingement, turbulator and pin fin cooling are used to further extract heat from the inner airfoil.

External cooling, known in the industry as film cooling, injects a coolant onto the outer airfoil surface at desired locations along the airfoil. Film cooling features (12) on the leading edge of airfoil, the region of the airfoil that has the highest heat transfer rate, are known in the industry as showerhead holes (11). Cooling features on the concave and convex sides of the airfoil are known as pressure (15) and suction (13) holes respectively. Cooling features on the trailing edge (17) of the airfoil are usually known as trailing edge slots. Cooling features on the tip (14) of the airfoil are known as either tip or squealer holes depending upon their location. Film cooling protects the blade's airfoil surface directly at the immediate and downstream injection region, as opposed to internal cooling techniques. To a lesser degree, film cooling provides additional heat removal from the airfoil by convection as the coolant flows through the wall of the airfoil.

Referring to FIG. 3, it is the size, shape and location of the immediate injection region that is named the film cooling effect (40). One should recognize that if the film cooling effect is too small, a result of either a reduction in the mass of coolant flowing through the cooling feature or defective cooling feature geometry, the blade's lifespan is decreased. Furthermore, if the film cooling effect is severely out of location, the blade's life span will be decreased. As in the case of an aircraft engine, this decreased lifespan could result in the loss of life. Therefore, the size, shape, and location of the cooling effect are critical design characteristics for the turbine blade. One should readily recognize from this discussion that the design intent of cooling features is the film cooling effect, and not the incidental characteristics such as its geometry, location and mass flow rate.

The prior art of methods for measuring a film cooling effect vary greatly between the environments of research and development, and manufacturing of gas turbine components. Research and development methods are distinguished by their enormous instrumentation, operational costs and considerable amount of time needed to accomplish a measurement. Manufacturing methods are characterized as being cheaper and quicker, but do not directly measure the film cooling effect and rarely measure every individual film cooling feature which would require isolation from the remaining plurality of features.

Research and development methods use designed experiments on actual components or simplistic models. The experiments are designed to measure the heat transfer coefficient, mass transfer analogy or film effectiveness of cooling features. Heat flow gauges, thin foil heaters with thermocouples, copper plate heaters with thermocouples, naphthalene sublimation, foreign gas concentration sampling, swollen polymer, ammonia diazo, pressure sensitive paint, infrared thermography, thermographic phosphors, liquid crystal thermography, hot and cold wire anemometry, laser doppler velocimetry, particle image velocimetry, laser holographic interferometer and surface visualization are some of the most common used in the industry. The cost and time associated with using these methods prohibit their use in a manufacturing environment.

Known manufacturing methods infer measurement of a film cooling effect by a combination of measurements. For example, measurement of the dimensional geometry and location of the cooling feature is combined with the measurement of the mass rate of air flowing through the cooling feature. Modern film cooling features are designed to have compound angles and complex shapes, complicating dimensional measurements. Turbine blades in particular may need hundreds of cooling features, complicating the flow measurement of an individual feature. As such groups of features are isolated and the collective mass rate of airflow measured.

All of these manufacturing methods are repetitive, time-consuming and rely on human intervention. Regardless of the manufacturing method used, the film cooling effect is never directly measured, but inferred from the combination of incidental measurements.

As can be recognized, there is the need for a new method that can automatically measure a film cooling effect faster, more precisely, and less expensively than known methods. Embodiments of the invention herein described solve these and other limitations in the prior art.

SUMMARY OF THE INVENTION

The present invention is a method that accurately and quickly measures an individual film cooling effect generated by a film cooling feature that extends from the hollow cavity within the structure of a gas turbine blade to the outer surface of this structure. With the inspection method of the present invention, the film cooling effect for an individual feature is easily measured without the need for its isolation from the remaining plurality of features. The method of the present invention provides an automated process, thus removing the chance of human error and eliminating the prior labor intensive methods.

In a first embodiment the apparatus for measuring a film cooling effect is a distinct machine consisting of the coordinated assemblage of an airflow test machine and an infrared inspection machine. The airflow test machine contains a group of critical flow nozzles and associated sensors capable of measuring the mass rate of air flowing through the plurality of film cooling features fabricated in a blade. The airflow test machine further comprises of an upstream flow controller. The infrared inspection machine is an apparatus disclosed in U.S. Pat. No. 7,671,338, which is incorporated by reference in its entirety, with the addition improvements herein described. Common to the airflow test machine and infrared inspection machine is a flow fixture for holding a blade and a diverter valve that isolates the two machines.

In a second embodiment of the apparatus, the airflow test and infrared inspection machines remain discrete apparatuses that share access to a network database and the ability to process and store measurement data generated by the discrete machines.

The exemplary embodiment of the airflow test data acquisition method, first sets the upstream flow controller to a design specified flow condition. Then an assortment of pressures and temperatures is measured.

The exemplary embodiment of the airflow test quantification method, the actual mass rate of airflow is computed from the pressure and temperature measurements. Corrections are then applied to the actual mass rate of airflow to compensate for differences between the density of the air at ambient and standard day conditions.

The exemplary embodiment of the relative individual cooling effect data acquisition method, an infrared camera is first positioned to view a collection of cooling features. Once in position a controlled heat flux is applied to the outer surface of the airfoil. After a predetermined time, a controlled chilled gas pressure, coolant, is rapidly injected into the blade and discharged out a plurality of cooling features onto the outer surface of the airfoil. When the coolant is discharged onto the blade's hotter outer surface it generates an isolated film cooling effect to radiate near the cooling feature. Improperly formed features either have no cooling effect, or a significantly reduced effect. Throughout this data acquisition process the camera is operated to capture a series of infrared image frames at a named sample rate.

The exemplary embodiment of the relative individual cooling effect identification method begins with first acquiring the frame just prior to the release of the coolant (45) and next, the frame just prior to when the coolant flow is stopped. The difference between these two frames produces what is named the raw image. Within the raw image, a sub-array is defined. This sub-array defines the boundaries of pixels around where a group of cooling effects is expected to be. A pixel is a single temperature element in the raw image. Using a novel adaptive process, the sub-array is analyzed to identify film cooling effects within this array.

In the exemplary embodiment of the relative individual cooling effect classification method, if an individual cooling effect area is less than a statistically computed partial limit, the cooling effect area is set to equal zero and the effect is classified as missing. If the cooling effect area is greater than a statistically computed blob limit, the cooling effect area is set to equal zero and its effect is classified as missing. If no cooling effect is identified where a cooling effect is expected, then the individual cooling effect area is set to zero and its effect is classified as missing. Otherwise, the individual cooling effect is classified as thru and its area set to the pixel count of the identified effect.

In the exemplary embodiment of the absolute individual film cooling effect quantification method, the total cooling effect area is computed as the sum of the relative individual cooling effect areas. Then the proportion of an individual cooling effect area relative to the total cooling effect area is computed. Finally the measure of each film cooling effect is quantified as the product of its proportion of total cooling effect area, the corrected mass rate of airflow and a correction factor to compensate for differences in test conditions used to generate the infrared signature of the relative individual film cooling effect.

With the film cooling effect quantified, its measurement is then compared with the limit for the design intent. If the design intent is unknown, then a sample of known good quality blades is inspected using this invention and statistical limits computed for use in determining the degree of film cooling effect conformance.

These and other objects and advantages of the present invention will become more readily apparent during the following detailed description taken in conjunction with the drawings herein. This invention significantly improves the quality of gas turbine components at a reduced manufacturing cost and cycle time.

DETAILED DESCRIPTION OF THE INVENTION

Figure 1:
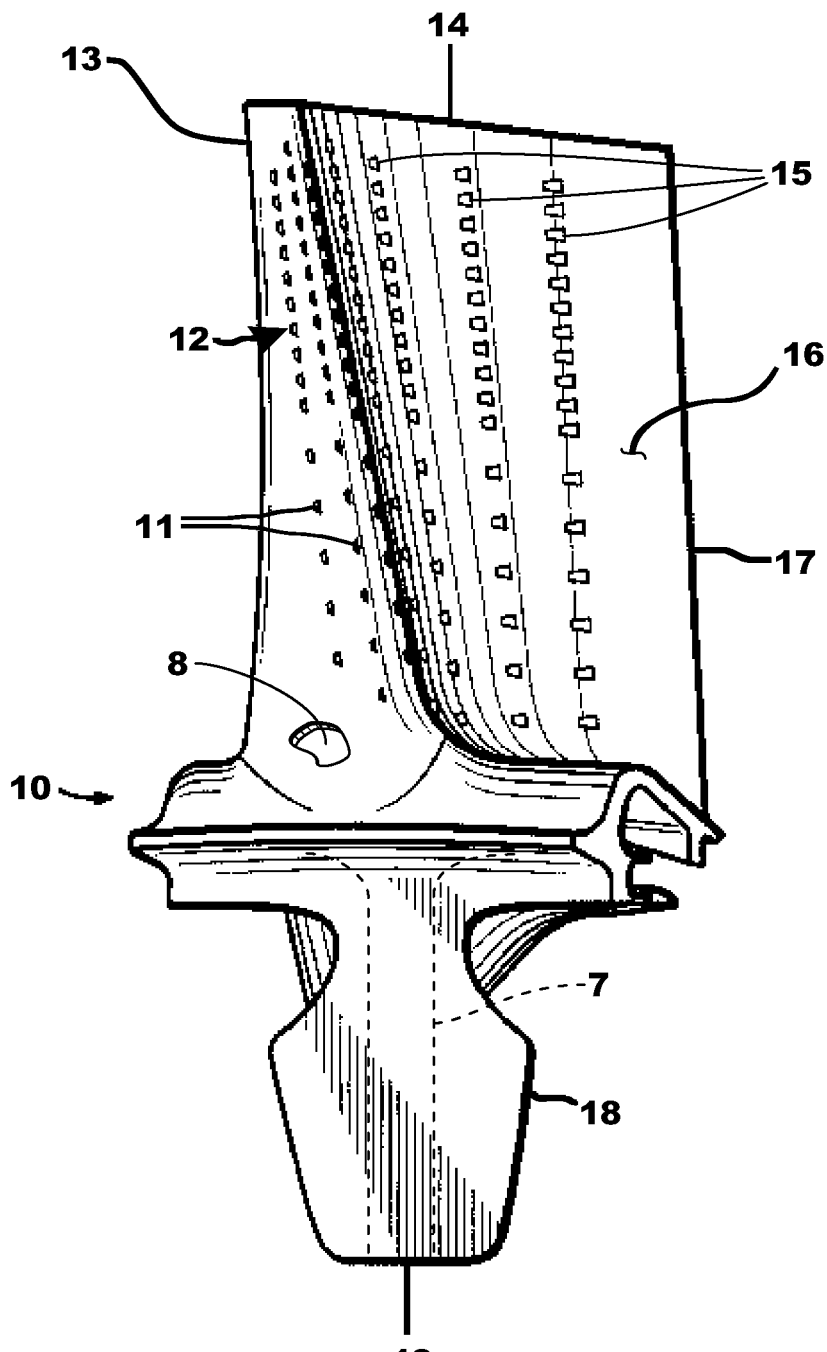
FIG. 1 is a partial perspective view of an example of a known, prior art turbine blade that utilizes rows of cooling features to generate a film cooling effect that must be inspected.
Figure 2:
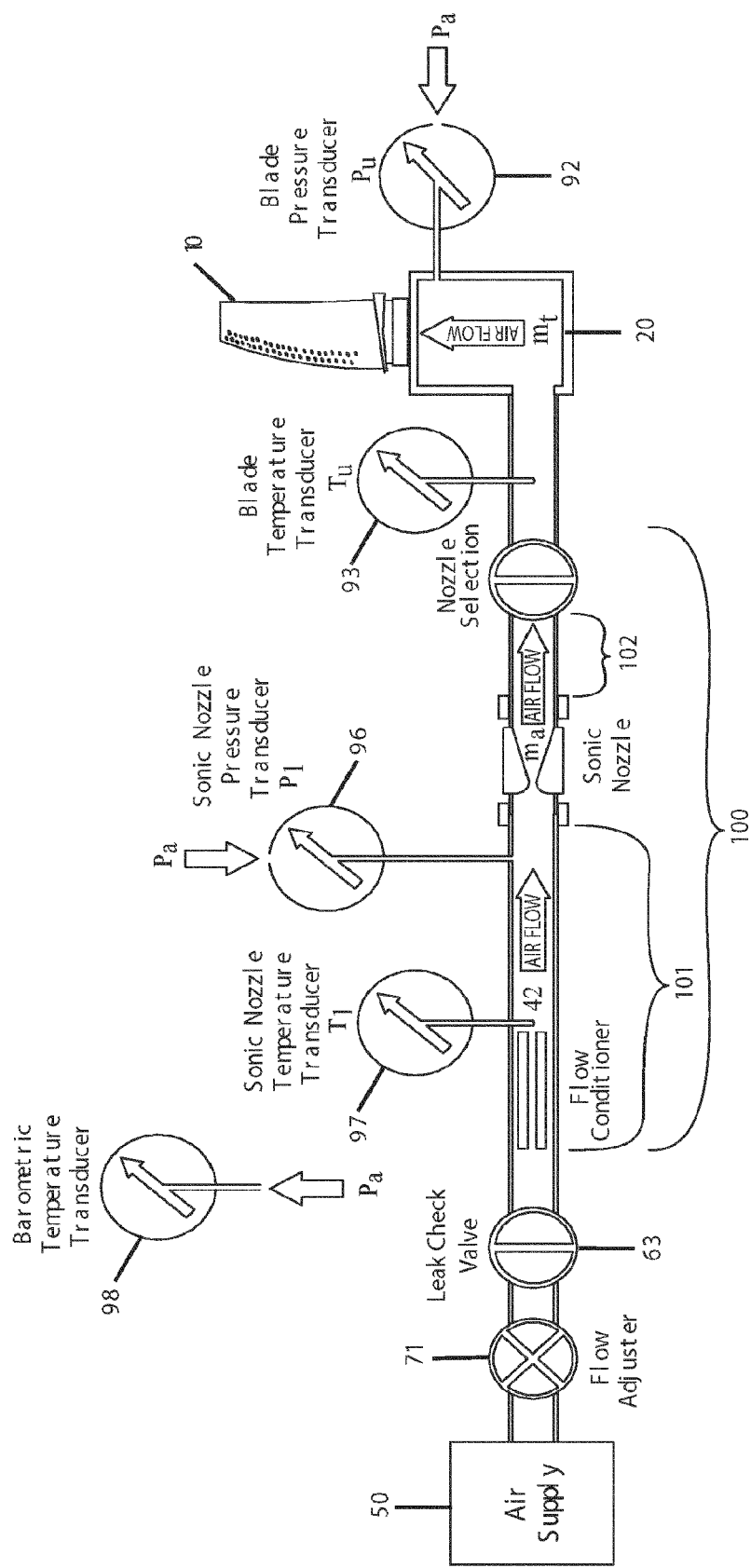
FIG. 2 is a simplified schematic diagram for a known, prior art airflow test system.

Referring to FIGS. 1, 3, 4, 5, 7, 7A and 7B, a first embodiment of an apparatus (30), the coordinated assemblage of both an airflow test machine (30a) and an infrared inspection machine (30b) is housed in the same cabinet (31). This apparatus (30), named a "film cooling inspection machine" is used to measure the film cooling effect (40) generated by film cooling features or openings (12) fabricated in a known blade (10). Common to both the airflow test machine (30a) and an infrared inspection machine (30b) is a flow fixture (20) for holding the blade (10) and a diverter valve (62) that isolates the two machines.

Figure 4:
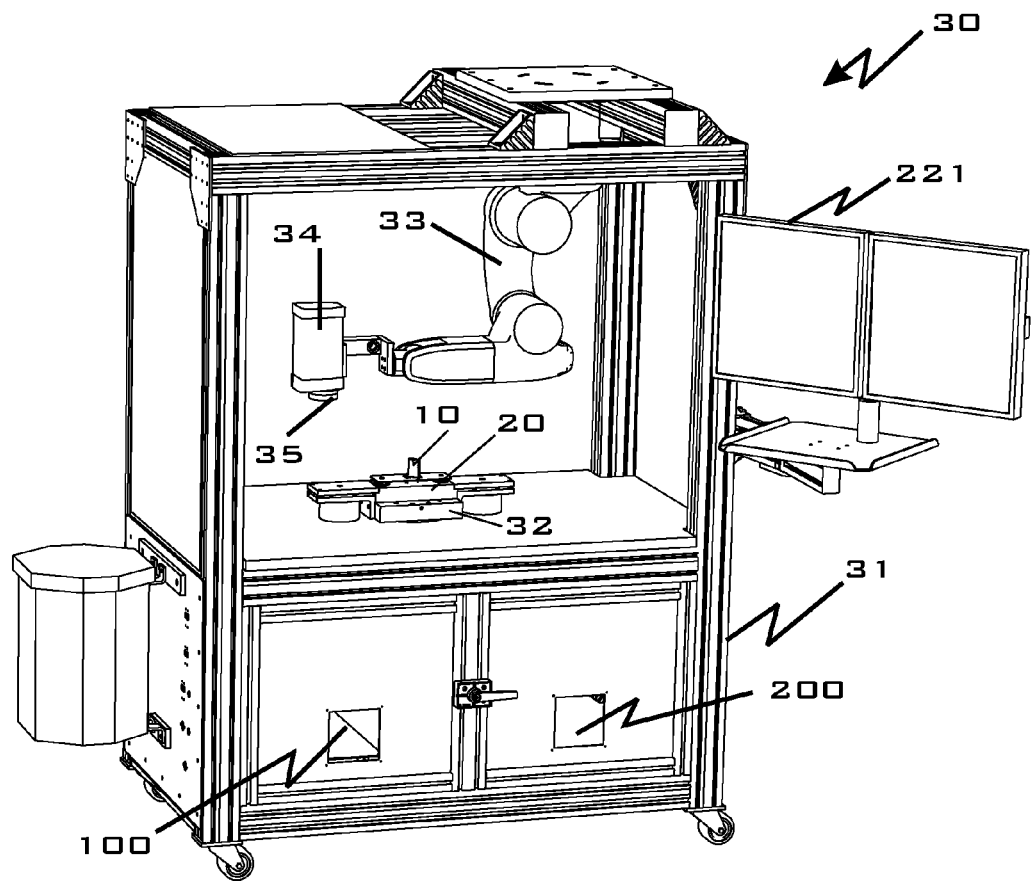
FIG. 4 is a perspective view of the embodiment of the apparatus for measuring a film cooling effect generated by a film cooling feature in accordance with the principles of the present invention.
Figure 5:
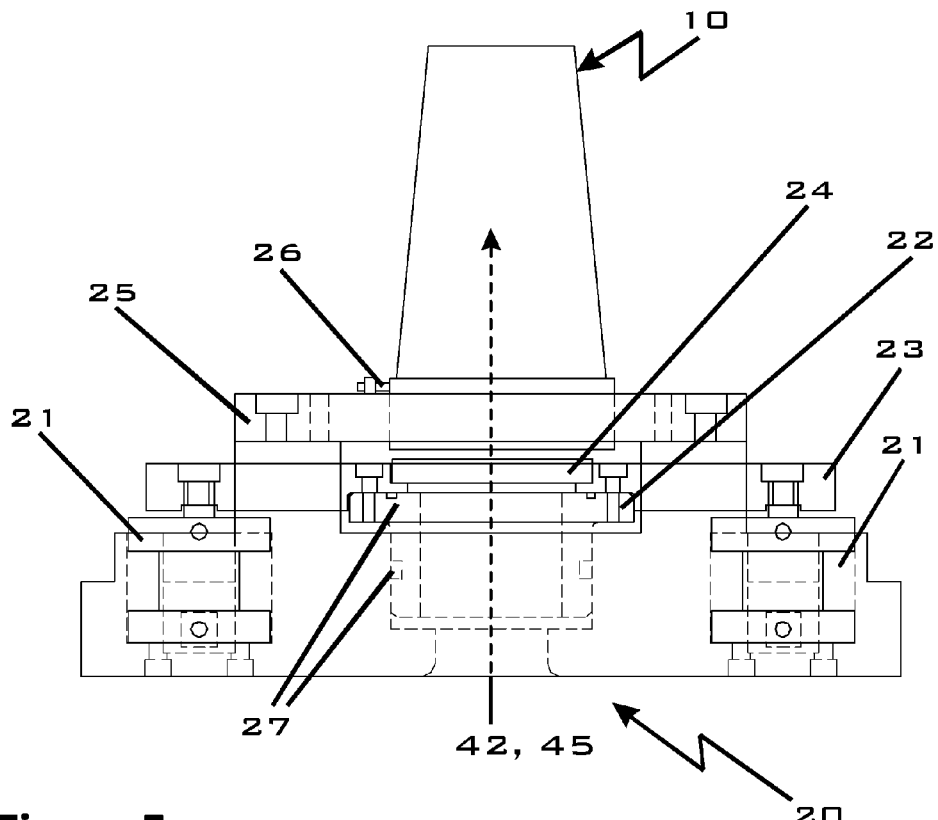
FIG. 5 is a front view of the exemplary embodiment of the flow fixture used to hold the gas turbine blade on the apparatus of FIG. 4.
Figure 6:
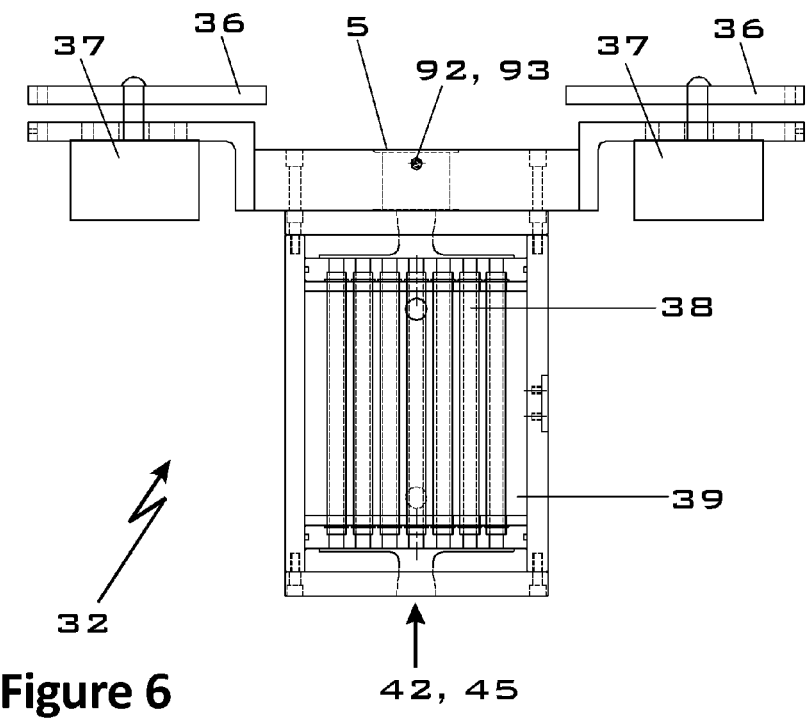
FIG. 6 is a front view of the exemplary embodiment of the plenum fixture used to hold the flow fixture and provide a second chilling of the coolant mounted in the embodiment of FIG. 4.

Referring to FIGS. 1, 4, 5, 6, 7 and 9, the blade (10) to be inspected is supported in the blade adapter plate (25), as best shown in FIG. 5. This adapter plate (25) is held in place on top of the flow fixture (20) which is mounted on top of the plenum fixture (32) which in turn is mounted in the middle of the cabinet (31) of the film cooling inspection machine (30), as shown in FIG. 4. The plenum fixture (32) is a cylindrical chamber with its inside diameter sized such that the velocity of the gas (42, 45) flowing inside is less than 0.02 Mach number at pressure of 14.8 pounds per square inch absolute (PSIA) and a flow rate of 0.03 mass pounds per second (Lbm/sec). The top face of this plenum fixture (32) has an O-ring seal (5) that mates with the bottom of the flow fixture (20). The majority of the length of the plenum fixture (32) is constructed as a flow conditioner comprising tubes (38) which also serves as a second heat exchanger to chill the gas forced through tubes (38). The chiller's (85) cooled process coolant (88) is allowed to circulate in the space (39) around the flow tubes (38) as shown in FIG. 6. Located near the top of the flow fixture (20) is both temperature (93) and pressure (92) sensors. These sensors measure the thermal dynamic properties of the gas (42, 45) injected into the hollow cavity (8) of the blade (10) being inspected. This gas, either coolant (45) or air (42), is fed to the chamber by the common port of a diverter valve (62). As shown in FIG. 6, flow fixture (20) is held in position on top of the plenum fixture (32) by two air cylinders (37) and clamps (36) that can be actuated manually and has its position sensed by the adapter load sensor (95). The signal from the adapter load sensor (95) is connected to the control (200) in such a manner that the signal can be programmed to keep the upstream pressure from being applied to the plenum fixture (32) when the flow fixture (20) is not properly loaded.

Figure 10A:
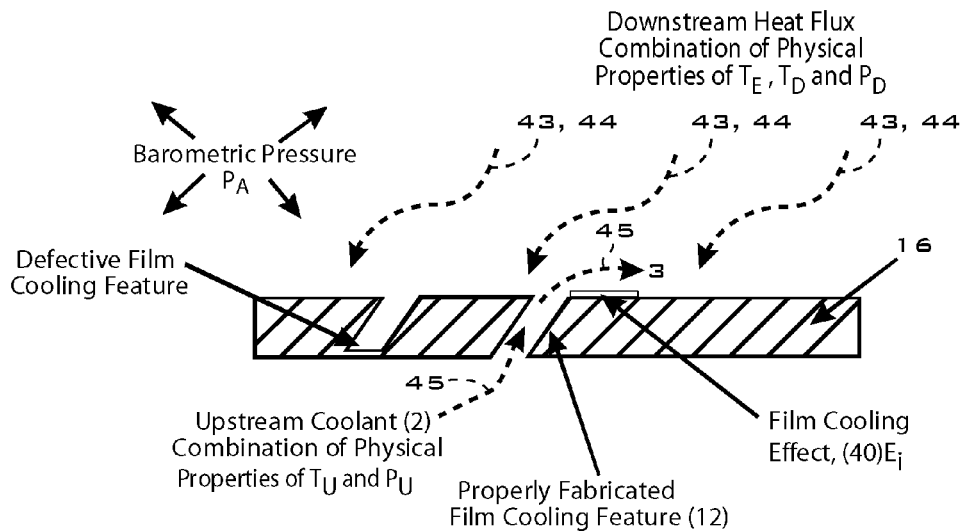
FIG. 10A is a detailed diagram of a film cooling effect measured by the present invention, shown as a longitudinal section of the blade.
Figure 10B:
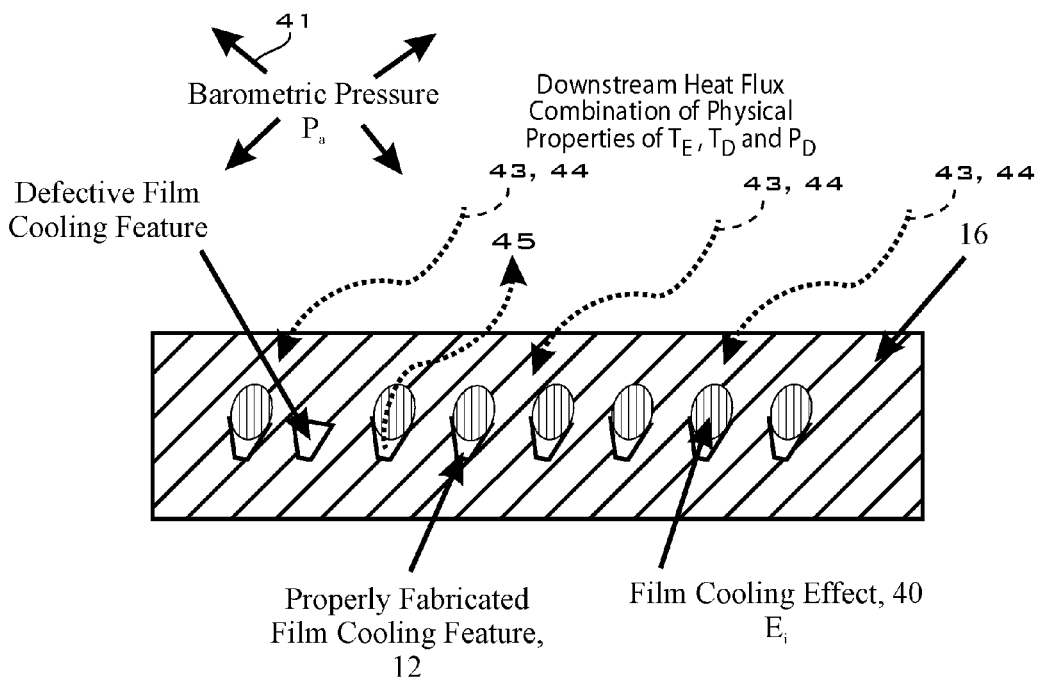
FIG. 10B is a detailed diagram of a film cooling effect measured by the present invention, shown as viewed from the skin of the blade.

Referring to FIGS. 1, 10A and 10B, for purposes of this description, when not otherwise specified, pressures and temperatures are named upstream and downstream with respect to its position relative to the film cooling feature (12) being inspected. Upstream refers to the gas (2) inside the blade's hollow cavity (8). See (2) of FIG. 10A. Downstream refers to the gas (3) outside the blade's hollow cavity (8). See (3) of FIG. 10A.

Figure 7:
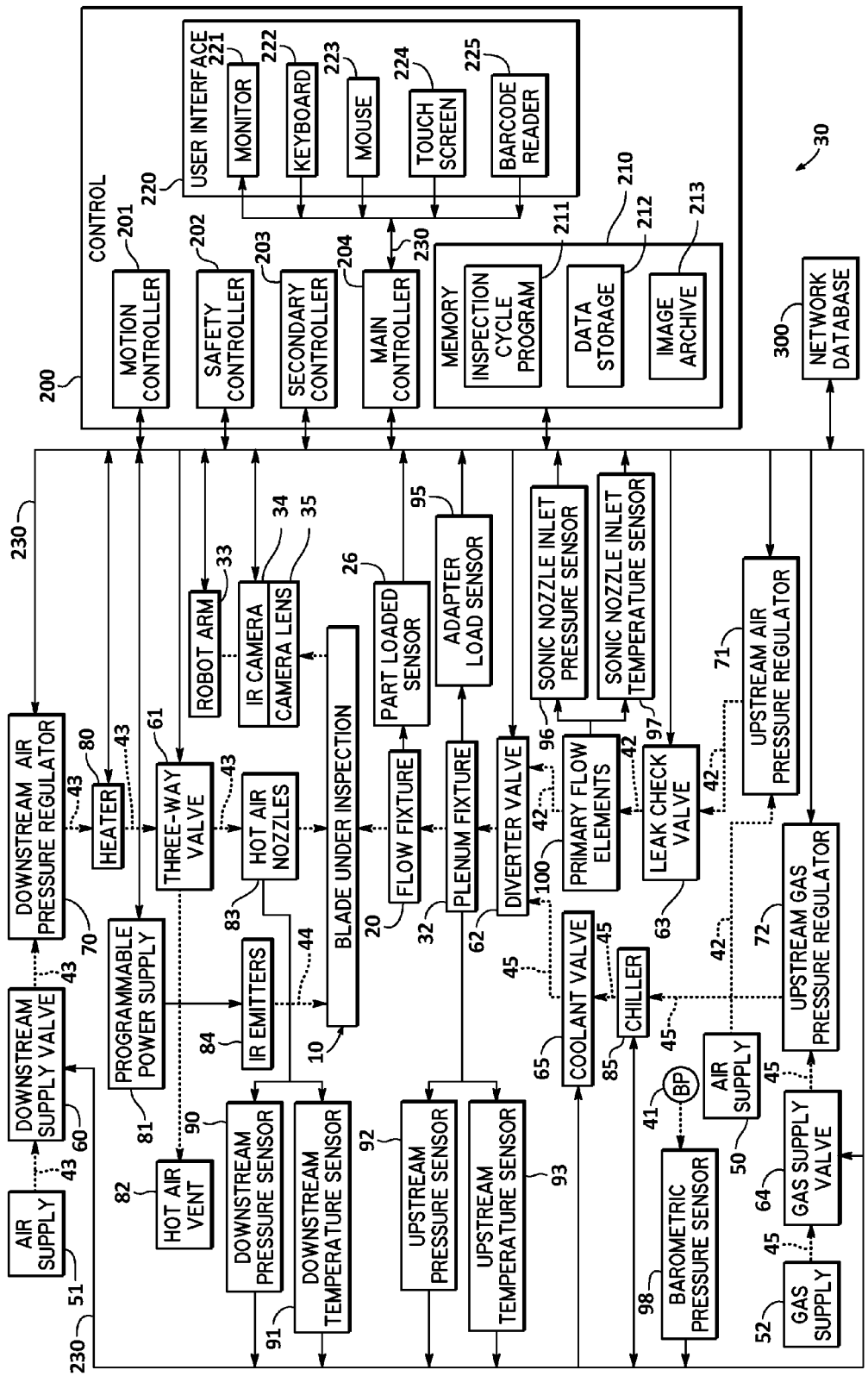
FIG. 7 is an overall block diagram for the exemplary embodiment of the apparatus of FIG. 4.

Referring to FIGS. 1, 5 and 7, the blade (10) is held at a stationary position on the flow fixture (20) by a removable adapter plate (25) that locates on the blade's root (18). The blade (10) has an opening (7) through the root (18) which leads to an internal cavity (8). In the middle of the flow fixture (20) a cylinder (22) pushes plate (23) to position a seal (24) onto the bottom of the blade's root (18) to form a leak tight conduit that is used to inject a coolant (45) or meter air (42) into the cavity and out of the plurality of film cooling features (12). O-ring seals (27), shown in FIG. 5, are used around the side and on the top of the cylinder (22) to provide a leak tight conduit for the upstream gas (42, 45). This cylinder (22) is moved by action of two smaller cylinders (21) located on the sides of the flow fixture (20). A part loaded sensor (26), in this embodiment, is a proximity sensor, mounted on the adapter plate (25) and used to verify the blade is properly loaded. The signal from this sensor is connected to the control (200) in such a manner that the signal can be programmed to keep the robot arm (33) from moving if the blade is not properly loaded. The geometry of the adapter plate (25) and seal (24) depends upon the particularities of blade being inspected. The adapter plate (25) and seal (24) can be easily removed and replaced with a distinctive, different set for a different blade.

Figure 7A:
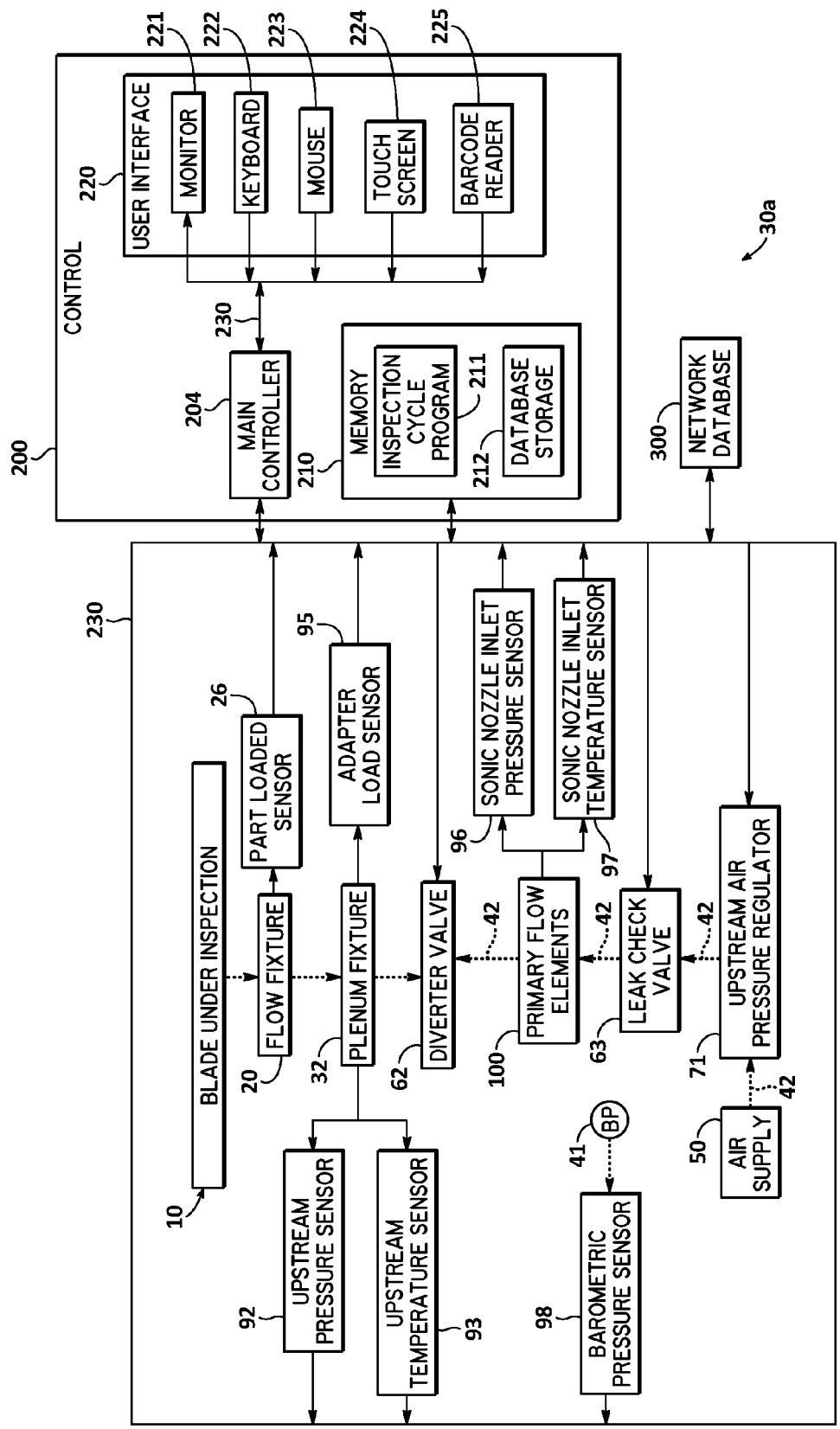
FIG. 7A is an overall block diagram for the exemplary embodiment of the airflow test machine of FIG. 4.
Figure 8:
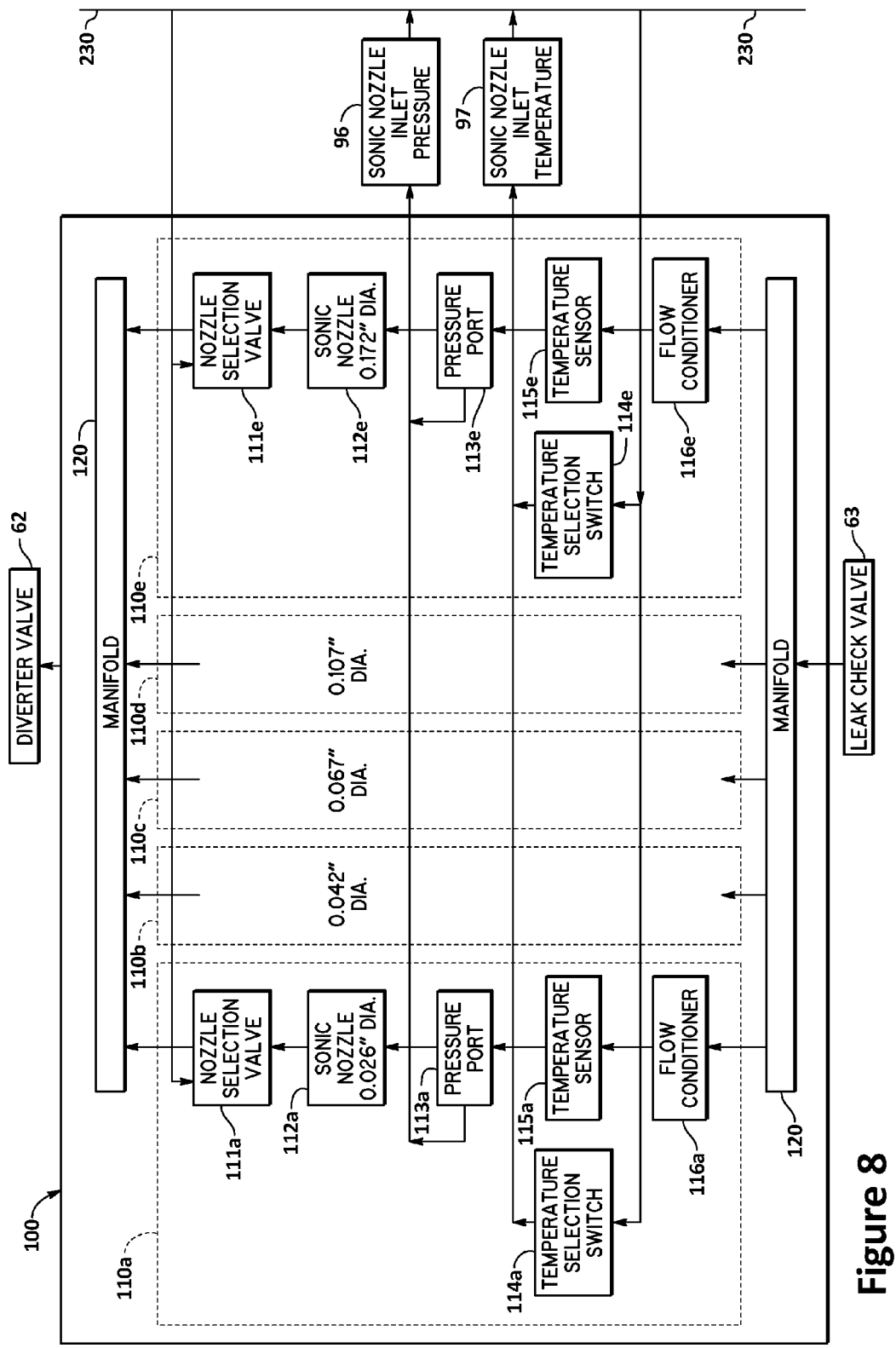
FIG. 8 is a block diagram for the exemplary embodiment of the primary flow element assembly for the embodiment of FIG. 7.

Referring to FIGS. 2, 4, 7A and 8, in one exemplary embodiment of the airflow test machine (30a), a group (100) of primary flow modules (110a-110e), best shown in FIG. 8, is mounted inside the cabinet (31). Each module (110a-110e) is designed such that it can plug into a manifold (120). This characteristic makes it easy to calibrate the full flow range of the primary flow module by removing it from the inspection machine (30) without being a labor intensive task. Each primary flow module (110a-110e) comprises an approach tube (101), a critical flow nozzle (112a-112e) and an exit tube (102). See FIG. 2. A critical flow nozzle is commonly known in the industry as a "sonic nozzle". Each approach tube contains a flow conditioner (116a-116e), whose purpose is to restore the velocity profile of the air (42) flowing through the approach tube to an acceptable reference condition; a temperature tap with associated temperature sensor (115a-115e) for measurement of the temperature of the air upstream of the sonic nozzle and a piezometer ring pressure tap (113a-113e) for measurement of the pressure of the air upstream of the sonic nozzle (112a-112e). The other end of the approach tube is connected to the sonic nozzle (112a-112e). The sonic nozzle may be one of several commercially available, for example a sonic nozzle commercially available from Flow-Maxx Engineering Inc. of North Richland Hills, Tex. The internal construction of a sonic nozzle comprises a converging inlet section, a minimum area throat, and a conical diverging diffuser section. As air flows through the converging section of the nozzle, the inlet pressure is converted to velocity. The diffuser slows the air down reconverting the velocity back to approximately its original pressure. When the pressure drop across the nozzle is increased, as the inlet pressure is held constant, a point will be reached where no further increase in the pressure drop is encountered, thus no further increase in mass rate of flow. At this point air flowing in the nozzle is choked and the velocity at throat diameter is equal to the speed of sound of the air, hence the name sonic nozzle. Under this condition, the mass rate of airflow, $m_a$, is principally dependent upon the pressure $P_1$ and temperature $T_1$ upstream of the nozzle. Downstream pressure changes will not affect the flow rate, and thus provides an accurate means of metering flow rates provided the critical choking pressure ratio is met or exceeded. The choke ratio is stored in the network database (300) for each nozzle and is recalled by the control (200) as needed by the inspection cycle program (211) to ensure the nozzle is operated in a choked mode. Each sonic nozzle has a different throat diameter, providing a different capability of flow rates. In this exemplary embodiment, the throat diameters are 0.026, 0.042, 0.067, 0.107 and 0.172 inch, each one chosen to allow the range of flow rate to overlap adjacent sonic nozzles. Connected to the diffuser end of the sonic nozzle is a valve (111a-111e) used by the control to select the needed sonic nozzle. The other end of each of these valves is attached to an exit port of manifold (120). The embodiment of this airflow measurement system is capable of measuring airflow rates in the range of 0.0003 to 0.0680 mass pounds per second (Lbm/sec).

Figure 7B:
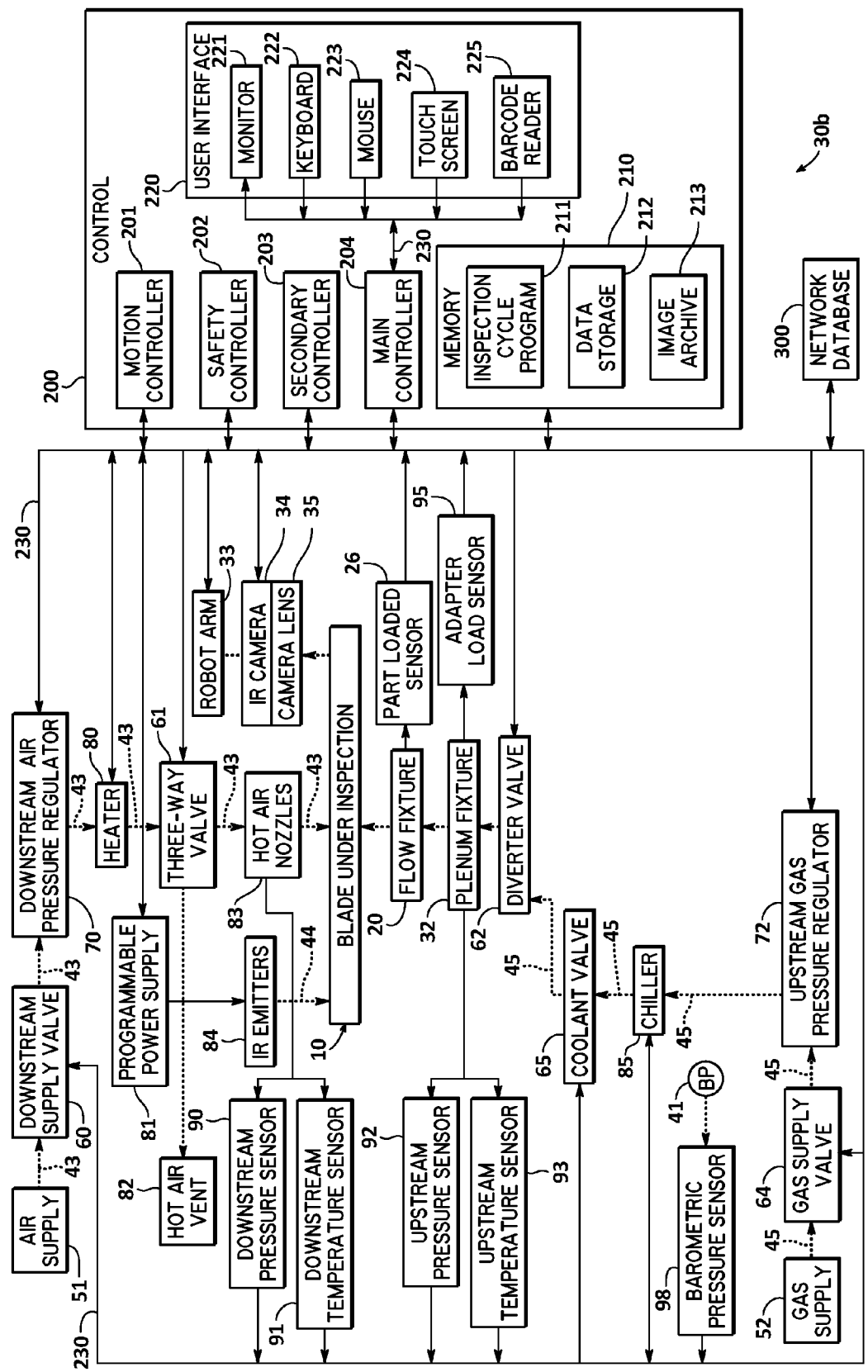
FIG. 7B is an overall block diagram for the exemplary embodiment of the infrared inspection machine of FIG. 4.

Referring to FIGS. 4 and 7B, in the exemplary embodiment the infrared inspection machine is as described in U.S. Pat. No. 7,671,338, with improvements described herein.

Referring to FIG. 7, for purposes of this description, a "position" shall refer to a spatial point, for example, the center point of the infrared camera lens (35) that is located with respect to a dimensional coordinate system, as described in U.S. Pat. No. 7,671,338. The coordinates x, y, z, rx, ry and rz are stored in a network database (300) and is recalled by control (200) as needed by the inspection cycle program (211). The control (200) has a plurality of controllers (201, 202, 203, 204 and 210) that may be embodied in programmable hardware and/or software. The particular embodiment of the control is a matter of design choice. The network database (300), main controller (204) and inspection cycle program (211) are in electrical communication with each other via the communication bus (230). This communication bus can be a combination of Ethernet, Firewire, USB, and other digital and analog signals.

Referring to FIGS. 7A and 7B and equations 12, 13 and 26, in a second embodiment of the apparatus, the airflow test and infrared inspection machines (30a, 30b) are discrete machines. In this embodiment, once both the mass rate of airflow, $m_s$ or $m_c$, and relative individual cooling effect, $A_i$, have been measured, the absolute individual film cooling effect $E_i$, is determined by the method described herein, except the mass rate of airflow and relative individual cooling effect area are recalled from the network database (300), prior to executing the herein described quantification process. This quantification process is coded in an appropriate inspection cycle program and executed on a control to produce the end result described herein. This control may be contained in either systems, or an independent control that has access to the network database.

Figure 3:
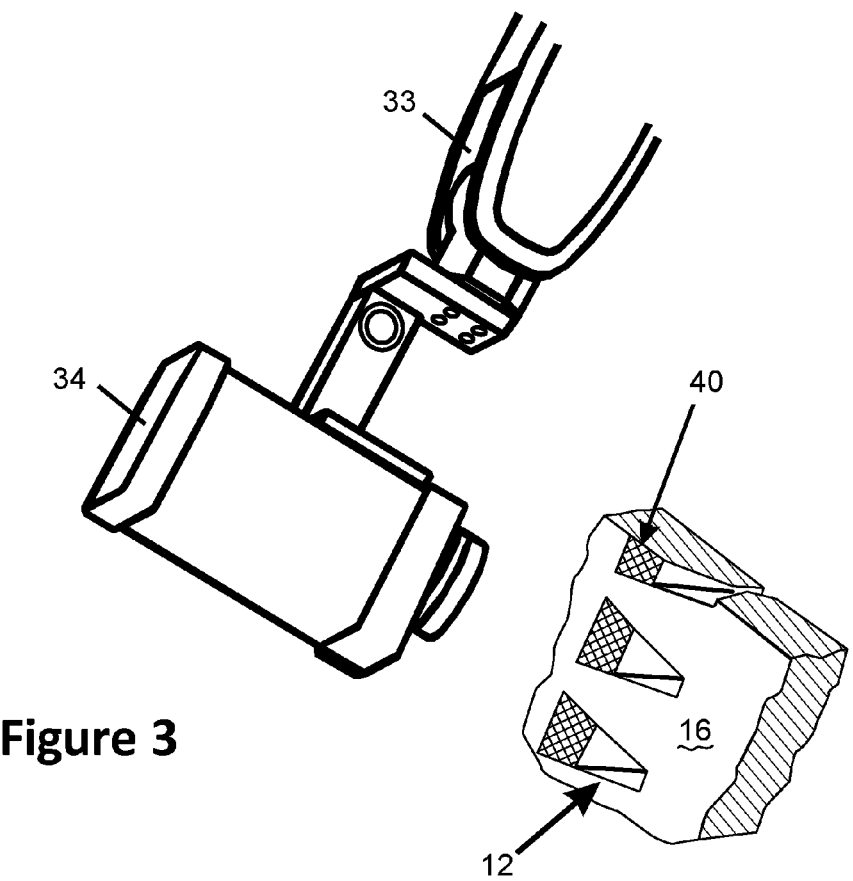
FIG. 3 is an illustration of the infrared signature generated by a film cooling effect on the skin of a blade near a shaped film cooling feature.
Figures 11, 15:
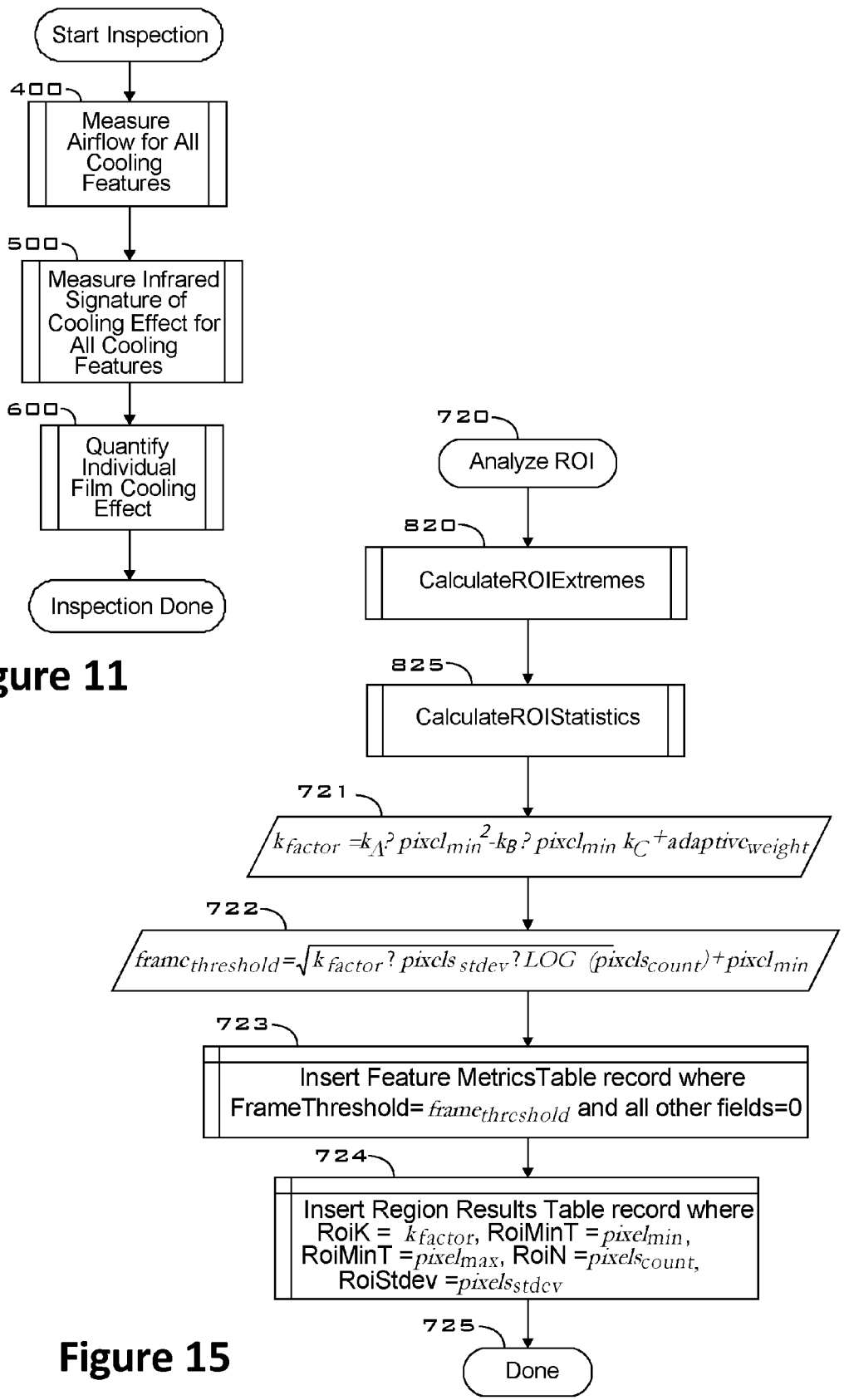
FIG. 11 is an overall flow chart of the exemplary embodiment of the method used to measure the film cooling effect generated by a film cooling features using the embodiments of FIGS. 4, 5, 6, 7, 8, 9, and 10.
FIG. 15 is a flow chart of an exemplary embodiment of the method for analyzing pixels located within a region of interest by the embodiment of the FIG. 14 method.

Referring to FIGS. 3 and 11, in the exemplary embodiment of the absolute measurement method to measure the film cooling effect (40) of individual cooling features (12), the inspection cycle starts by first measuring the mass rate of air (42) flowing through the plurality of cooling features (400). The infrared signature of the relative film cooling effect is measured (500) for the plurality of cooling features (12). The precise order of steps 400 and 500 is unimportant and can be performed in any order. The final step (600) quantifies the individual relative film cooling effect by combining the measurements obtained in steps 400 and 500.

Figure 12:
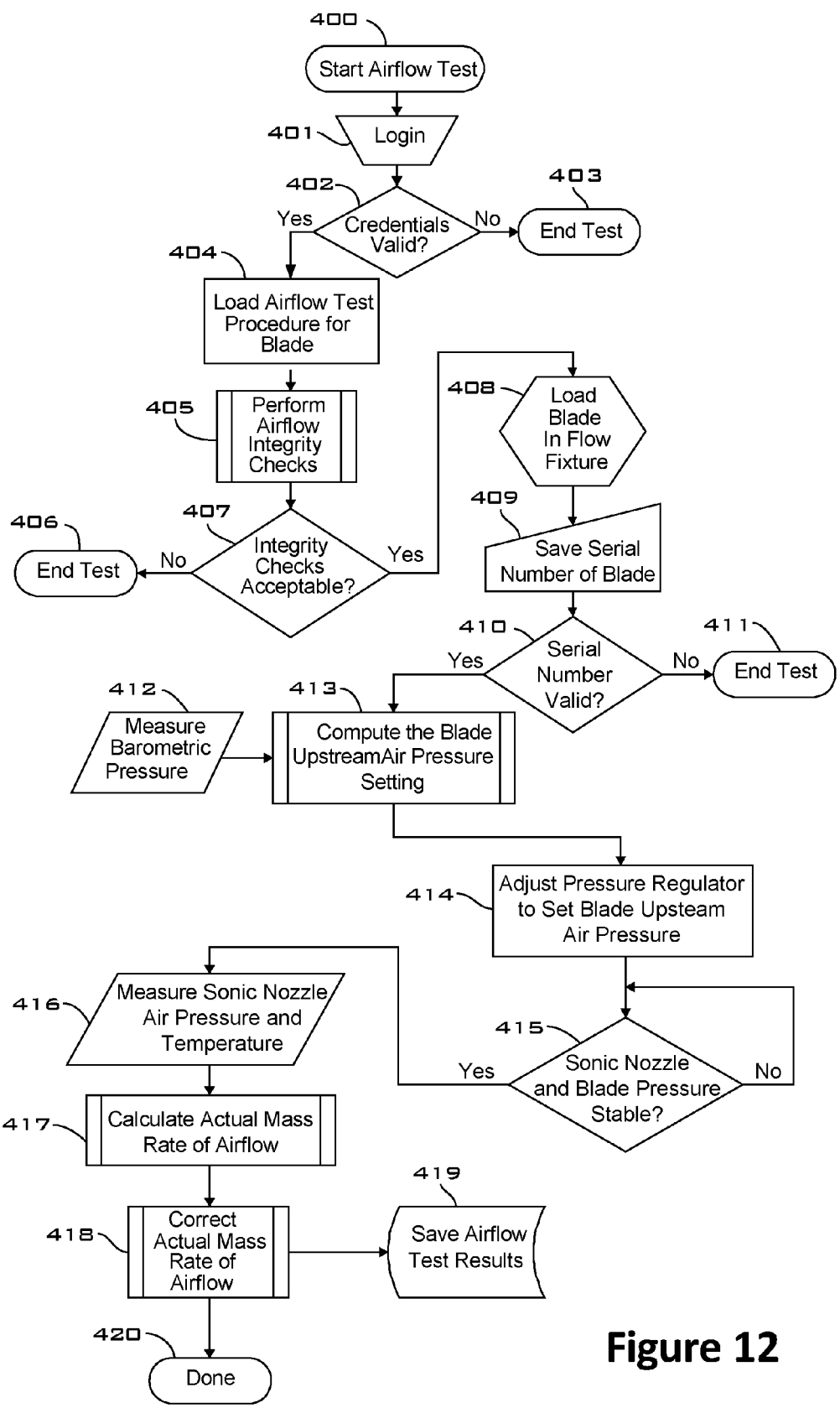
FIG. 12 is a flow chart of the exemplary embodiment of the method for measurement of the mass rate of air flowing through the plurality of film cooling features for the embodiment of the FIG. 11 method.

Referring to FIGS. 1, 7A and 12, in the exemplary embodiment of the airflow test method (400), the proper inspection cycle program (211) is executed. Immediately, the inspector is prompted to enter their login credentials (401), which are validated (402) before proceeding. Upon being properly validated, the operator is prompted to select the proper airflow test procedure (404) for the blade being inspected. If the credentials are not validated, the inspector is alerted and the inspection cycle program is aborted (403). Depending upon the blade's design, a series of integrity checks (405) may be needed to be successfully performed prior to measuring the mass rate of air flowing through the cooling features (12) of the blade (10). These checks may include a leak check valve (63), various other leak checks, seal flow restriction checks and airflow master check. Upon completing all needed integrity checks, the acceptability (407) of these checks is tested by control (200). If the needed integrity checks fail, the inspector is alerted and the inspection cycle program is aborted (406). With all needed integrity checks successfully performed, the blade to be tested is loaded (408) into the flow fixture (20). The operator is then prompted (409) to enter the serial number of the blade to be tested. If the serial number is validated (410) as associated with the airflow test procedure (404), the airflow data acquisition method begins. If the serial number is not properly validated, the inspector is alerted and the inspection cycle program is aborted (411).

Referring to FIGS. 1, 7A, 8, 10A and 12, in one exemplary embodiment of the first airflow test data acquisition method, the control (200) commands the barometric pressure, $P_a$, sensor (98) to measure (at block 412) the barometric pressure (41) (identified schematically as "BP" in FIG. 7A) downstream of the blade (10) and is stored in the data storage memory (212) for later use. The control then commands one of the sonic nozzle selection valves (111a-111e) to open, shown in FIG. 8. To determine which sonic nozzle (112a-112e) needs to be opened, the target mass rate of airflow, $m_x$, is first computed, as denoted by equation 1, as the mean flow rate between the upper, $AF_u$, and lower, $AF_l$, design airflow limits, recalled from the network database (300).

$$m_x = \frac{AF_u + AF_l}{2} \qquad \text{Equation 1}$$

Referring to FIGS. 7A and 8, the control (200) compares $m_x$ against the flow range, $m_z$, of each of sonic nozzle (112a-112e) to obtain the one that has the closest flow rate at a nominal inlet pressure, $P_1$, of 55 PSIA. $m_z$ is computed by the control as denoted by equation 2, where the slope, $s_1$, and offset, $o_1$, are determined during the calibration process of the sonic nozzle as stored in the network database (300). $s_1$ and $o_1$ are solved by linear regression from the calibration data set of $P_1$ and the associated airflow rate of the sonic nozzle at $P_1$. If the flow rate of a single sonic nozzle is not capable of achieving the nominal flow rate, then as described in another embodiment, a combination of sonic nozzles is selected by the control.

$$m_z = s_1 \times 55 + o_1 \qquad \text{Equation 2}$$

Referring to FIGS. 1, 7A, 8 and 12, with the needed sonic nozzle (112a-112e) selected, the control (200) commands the leak check valve (63) to open in a position that will allow air (42) from a source of pressurized air (50) to flow through a first "upstream air" pressure regulator (71), the inlet manifold (120), the selected flow conditioner (116a-116e), the selected temperature sensor (115a-115e), the selected pressure port (113a-113e), the selected sonic nozzle (112a-112e), the selected nozzle selection valve (111a-111e), the manifold (120), the fixture selection valve (62), the plenum fixture (32), the flow fixture (20), the flow fixture seal (24) the opening (7) at the base (19) of the blade (10), the internal cavity (8) of the blade (10) and allowed to discharge through the plurality of cooling features (12) that are being measured. The control (200) commands the sonic nozzle pressure sensor (96) to measure $P_1$ present at the pressure port. $P_1$ is measured with a 0-100 pounds per square inch gauge (PSIG) pressure transducer. The control (200) commands the first "upstream air" pressure regulator (71) to set the upstream pressure, $P_u$, measured by the upstream pressure sensor (92) to the design airflow constant pressure ratio, $PR_f$, computed (413) as denoted by equation 3 using the measurement of $P_a$, and $PR_r$. $PR_r$ is typically in the range of 1.01 to 2.0. The upstream pressure sensor (92) provides the first pressure feedback signal. The control (200) uses the first upstream pressure sensor feedback signal and a known fuzzy logic algorithm in the control to set $P_u$ (414) to obtain $PR_r$ by adjusting $P_1$. Once $P_u$ is set within the needed reference setting window, $W_r$, and both $P_1$ and $P_u$ pressures are stable (415), in FIG. 12, as determined by a known algorithm, the mass rate of air flowing through the plurality of cooling features (12) is computed as later described. Conversely, if the pressures are not stable, the control waits a predetermined length of time and repeats (415) algorithm. The needed $PR_r$ and $W_r$ setting is stored in the network database (300) and is recalled by the control as needed by the inspection cycle program (211).

$$P_u = (PR_r - 1) \times P_a \qquad \text{Equation 3}$$

Referring to FIGS. 1, 7A, 8 and 12 with $P_u$ set within the $W_r$ and both $P_1$ and $P_u$ pressures stable, the control (200) commands the temperature selection switch (114a-114e) to close to a position that allows the temperature of the air (42) upstream of the selected sonic nozzle (112a-112e) to be measured (416) by the selected temperature sensor (115a-115e), $T_1$, and electrically communicated to the control (200) via the sonic nozzle inlet temperature sensor (97). Unless otherwise specified, all temperatures are expressed in absolute units of Rankine (R). The selected $P_1$ is measured (416) using the sonic nozzle inlet pressure sensor (96) and is also electrically communicated to the control. The control (200) algebraically adds this gauge pressure measurement to the $P_a$ to produce an absolute pressure measurement for $P_1$. Unless otherwise specified, all pressures are expressed in absolute units of PSIA. After measuring $P_1$ and $T_1$, the mass rate of airflow, $m_a$, is solved by an iteration algorithm processed by the control (200). The iteration solves the coefficient of discharge, $C_d$, of the selected sonic nozzle dependent upon the Reynolds number, $R_d$. $R_d$ is a figure of merit that describes the flow condition of air through the sonic nozzle and is computed (417), in FIG. 12, as denoted by equation 4. Observe equation 4 needs $m_a$, hence the use of an iterative algorithm. This algorithm starts by first computing the viscosity, $\mu$, as denoted by equation 5, of the air flowing through the selected sonic nozzle, where $T_k$ is $T_1$ in units of Kelvin. Then compute the sonic nozzle throat area, $A_n$, as denoted by equation 6, where d is the throat diameter of the selected sonic nozzle in units of square inch. Next compute the critical flow factor, $C_c$, as denoted by equation 7, where $P_{atm}$ is $P_1$ expressed in units of atmosphere. The prime Reynolds number $R_d'$, is initially set to a value computed as denoted by equation 8, where the slope, $s_2$, and offset, $o_2$, are determined during the calibration process of the sonic nozzle. $s_2$ and $o_2$ are computed by linear regression from the calibration data set of $P_1$ and associated Reynolds number of the sonic nozzle at $P_1$. The prime coefficient of discharge, $C_d'$, is initially set to $C_d$ computed as denoted by equation 10 using $R_d'$ and subtracting 0.001. Using $C_d'$ as $C_d$ and $R_d'$ as $R_d$ the initial mass rate of airflow is computed as denoted by equation 9. Using this $m_a$, $R_d$ is computed and then $C_d$ is computed as denoted by equation 10, where the fourth degree polynomial coefficients, $c_1, c_2, c_3, c_4, c_5$, are regressed from the calibration data set of the selected nozzle. If the absolute difference between $C_d'$ and $C_d$ is less than 0.0001 then the iteration is complete, otherwise $C_d'$ equals the just computed $C_d$ and a new $R_d$ is computed proceeded by computation of a new $C_d$ and new $m_a$. The previously described process is repeated until the iteration is completed when the airflow test process is done (420). The needed d, $s_1, o_1, s_2, o_2, c_1, c_2, c_3, c_4$, and $c_5$ settings were previously stored in the network database (300) and recalled by the control as needed by the inspection cycle program (211).

$$R_d = \frac{4 \times m_a}{\pi \times d \times \mu} \quad \text{Equation 4}$$

$$\mu = \frac{\left[\begin{array}{c} 12.185 + 0.03205 \times (T_k - 293.2) + \\ 0.01705 \times (P_{atm} - 1) \end{array}\right] \times 10^{E-6}}{12} \quad \text{Equation 5}$$

$$A_n = \left(\frac{d}{2}\right)^2 \times \pi \quad \text{Equation 6}$$

$$C_c = 0.68309 + 1.42025^{E-5} \times T_k - \\ 2.80046^{E-8} \times T_k + 3.47447^{E-5} \times (P_{atm} \times 101.3253) - \\ 1.80997^{E-7} \times (P_{atm} \times 101.3253) \times T_k + \\ 2.46278^{E-10} \times (P_{atm} \times 101.3253) \times (T_k)^2 \quad \text{Equation 7}$$

$$R_d' = P_1 \times s_2 + o_2 \quad \text{Equation 8}$$

$$m_a = \frac{A_n \times P_1 \times C_d \times C_c}{\sqrt{T_1}} \quad \text{Equation 9}$$

$$C_d = R_d^4 \times c_1 + R_d^3 \times c_2 + R_d^2 \times c_3 + R_d \times c_4 + c_5 \quad \text{Equation 10}$$

Referring to FIGS. 7A and 8, in a second exemplary embodiment of the airflow test data acquisition method, more than one sonic nozzle (112a-112e) is selected by the control (200), the previously described mass flow rate algorithm is repeated for each sonic nozzle selected and each $m_a$ is summed to produce a final $m_a$.

Referring to FIGS. 7A, 8 and 12, in the exemplary embodiment of the airflow test quantification method, $m_a$ is dependent upon the density of the air (42) at the time of measurement, and can only be duplicated under similar conditions. As such it must be normalized (418) to produce a value that is independent of ambient conditions. First the mass rate of airflow is corrected for differences between the air temperature upstream of the sonic nozzle (112a-112e) and blade (10) as denoted by equation 11. Next this corrected mass rate of airflow, $m_a$ is again corrected for sonic flow conditions as denoted by equation 12. If $PR_r$ is less than the critical pressure ratio for air, approximately 1.894, then an additional subsonic correction as denoted by equation 13 is solved. The total mass rate of airflow, $m_t$, is equal to either the sonic, $m_c$, or the subsonic, $m_s$, flow rate. This total mass rate of airflow along with all pressure and temperature measurements, and the serial number of blade are stored (419) in the network database (300) for later use.

$$m = m_a \times \sqrt{\frac{T_1}{T_u}} \quad \text{Equation 11}$$

$$m_c = m_a \times \frac{P_{ref}}{P_u} \times \sqrt{\frac{T_u}{T_{ref}}} \quad \text{Equation 12}$$

$$m_s = m_c \times \sqrt{\frac{\left(\frac{1}{PR_r}\right)^{1/0.7} - \left(\frac{1}{PR_r}\right)^{12/7}}{\left(\frac{P_a}{P_u}\right)^{1/0.7} - \left(\frac{P_a}{P_u}\right)^{12/7}}} \quad \text{Equation 13}$$

Referring to FIGS. 4, 5, 7B, 13A and 13B, in the exemplary embodiment of the measurement of the relative individual cooling effect (500), an inspection cycle program (211) is executed. Immediately, the inspector is prompted to enter their login credentials (501) using the user interface (220), which includes the monitor (221) (which is also shown mounted on the cabinet (31) in FIG. 4) the keyboard (222), mouse (223) or touch screen (224), which is validated (502) before proceeding. If the credentials are not validated, the inspector is alerted and the inspection cycle program is aborted (503). These credentials set a privilege level restricting the inspector from the ability to change inspection data stored in the network database (300). Upon being properly validated, the inspector then loads the needed blade inspection procedure (504) (referred to as "Inspection Procedure Blade" in FIG. 13A) by scanning (225) a bar code on a routing sheet accompanying the group of blades (10) to be inspected. The inspection cycle program then locates the proper inspection data from the network database and loads it into the main programmable control memory (212). Depending upon the blade's design, the correct adapter plate (25) is loaded (505) on to the flow fixture (20) by the inspector. With this tooling properly installed, the program directs the inspector to scan a bar code (225) on the adapter plate to verify (507) the correct tooling is in place, eliminating the possibility of human error. If the adapter plate is not valid for the selected blade inspection procedure (504), the inspector is alerted and the inspection cycle program is aborted (506). If the correct tooling is in place, the inspection cycle program continues execution (507). As needed a good and bad master is inspected (508). If the good and bad master inspections are successful, the operator is then prompted (509) to enter the serial number of the blade (10) to be tested. If the serial number is validated (510) as associated with the blade inspection procedure (504), the blade to be inspected is loaded (512) into the flow fixture (20). This information can again be entered by scanning a bar code on the blade or router sheet, eliminating the possibility of human error. If the serial number is not valid for the selected inspection procedure, the inspection cycle program is aborted (511). The inspection cycle program then verifies (514) the blade is loaded properly using information transmitted by part loaded sensor (26), eliminating the possibility of human error. If the blade is not properly loaded, the inspector is alerted and the inspection cycle program is aborted (513). With the blade properly loaded, the control (200) is operated to command (515) cylinders (21) to retract, moving the seal (24) up against the bottom (19) of the blade (10). The inspection cycle program then prompts the inspector to verify (517) the blade is securely in place. The inspector may respond by aborting the inspection cycle program (516) or respond (517) to begin the relative individual cooling effect data acquisition process. At any time during the inspection cycle, should the inspector or anyone else attempt to enter the enclosure (31) while the robot arm (33) is moving, the safety controller (202)

stops and aborts the inspection procedure. Once the inspection cycle program is complete, the inspector may inspect another blade or quit the inspection cycle program (547).

Referring to FIGS. 1, 3, 4, 7B, 13A and 13B, in one exemplary embodiment of the relative individual cooling effect data acquisition method, a position counter is set to zero (519), the position coordinates (521) are recalled from the database (300), and the infrared camera (34) is positioned (522) where its field of view is at an oblique angle with the center line of a cooling feature (12) and the cooling effect is in focus. When the robot arm (33) stops moving, the control (200) communicates to the motion controller (201) to verify the robot has stopped at the commanded position (524). If the robot is not in the commanded position (524(n)) at block (524), the inspector is alerted and the inspection cycle program is aborted (523). Conversely, at block (524) if the robot is in position (524(y)) and the commanded position is a "dummy" move (525), the control (200) increments the position counter (541) and the position counter is compared (520) with the number of position records stored within the blade inspection procedure (504). If the position counter is greater than the number of positions, e.g., (520(n)), the control (200) turns off all downstream conditions (542). If the position counter is less than the number of positions, e.g., (520(y)), the process continues to a step of getting the position coordinates (521) as described herein. Otherwise at block (525(n)), with the camera at the command location, the needed position and orientation with respect to the blade (10), the control (200) commands a downstream supply valve (60) and the three-way valve (61) to open in a position that allows air (43) from a source of pressurized air (51) to flow into heater (80). The control is electrically connected to the heater (80) and a first temperature sensor (91) provides a first temperature feedback signal. The control (200) uses the first temperature feedback signal and a known proportional-integral-derivative (PID) algorithm in the control to operate the heater (80) and by convection to bring the air temperature, $T_d$, to a range of 100 to 500 degrees Fahrenheit. The value used is determined in the later described setup procedure. A second pressure regulator (70) is electrically connected to, and operable by, the control (200) to set the heated downstream air pressure, $P_d$, measured by the second downstream pressure sensor (90) to the needed pressure ratio, $PR_d$, computed as denoted by equation 14 using the measurement (518) of $P_a$ sensor (98) and $PR_d$ in the range of 1.001 to 1.500. The value used is determined in the later described setup procedure. The second pressure sensor (90) provides the second pressure feedback signal. The control (200) uses the second pressure sensor feedback signal and a known PID algorithm in the control to set $P_d$. The needed $T_d$ and $PR_d$ settings are stored in the network database (300) for each position.

$$P_d = (PR_d - 1) \times P_a \qquad \text{Equation 14}$$

Figure 13A:
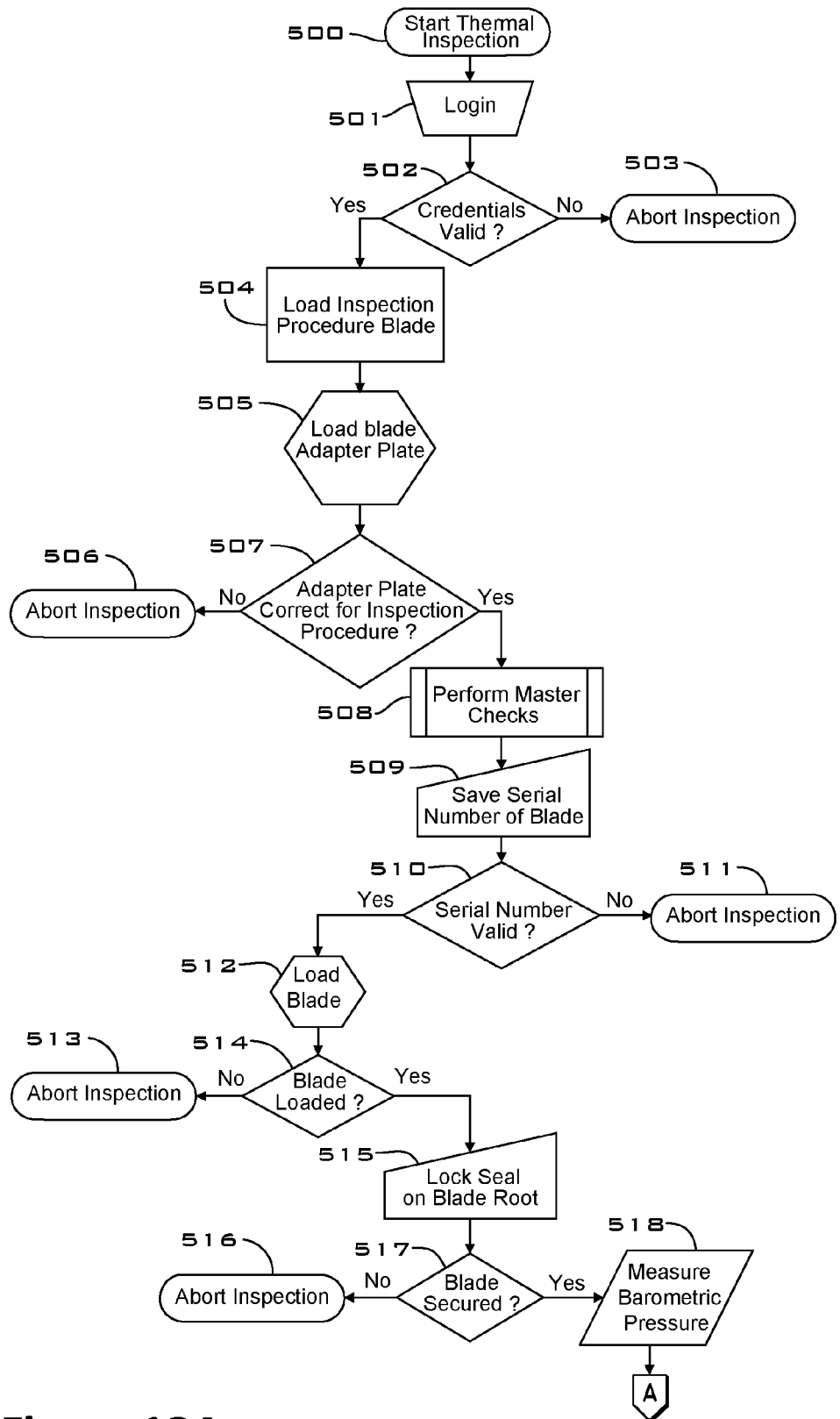
FIG. 13A is a flow chart of the exemplary embodiment of the method for measurement of the relative individual film cooling effect generated by a film cooling feature for the embodiment of the FIG. 11 method as continued in FIG. 13B.
Figure 13B:
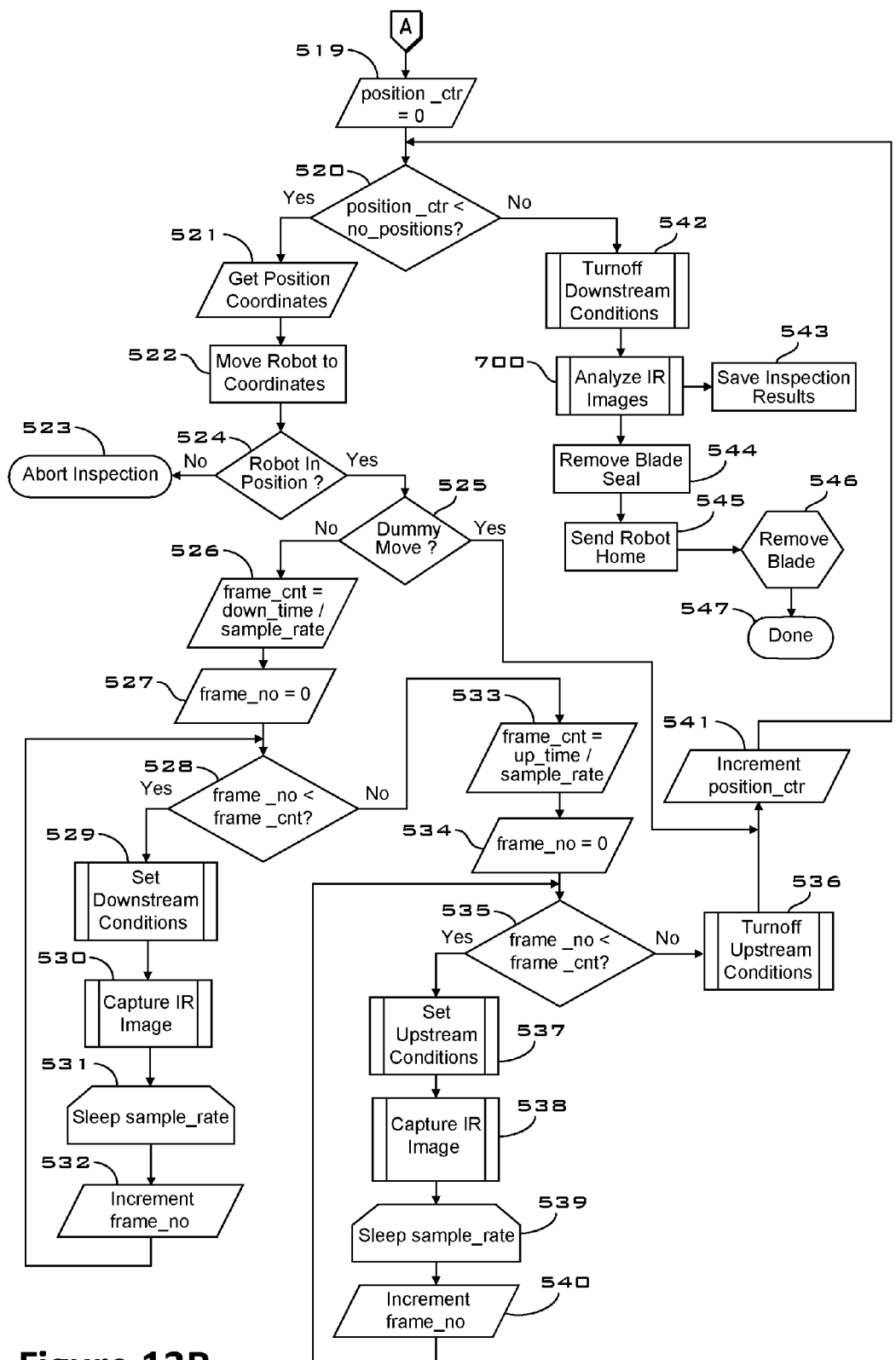
FIG. 13B is a continuation of the flow chart shown in FIG. 13A of the exemplary embodiment of the method for measurement of the relative individual film cooling effect generated by a film cooling feature for the embodiment of the FIG. 11 method.

Referring to FIGS. 1, 7B and 13B, this heated air (43) from air supply (51) passes through a group of nozzles (83) and is applied over an area of the blade's skin (16) that surrounds the cooling features (12) being inspected. When the heated air is not being applied the blade's skin, a three-way valve (61) diverts this air to the hot air vent (82). No further description of these nozzles or use of infrared emitters (84), $V_e$, and programmable power supply (81) are described herein, as their description is as claimed in U.S. Pat. No. 7,791,025, which is incorporated by reference in its entirety. The combination of heated air (43) and infrared emission (44) generates the heat flux or downstream conditions (which are set at block 529).

Figure 9:
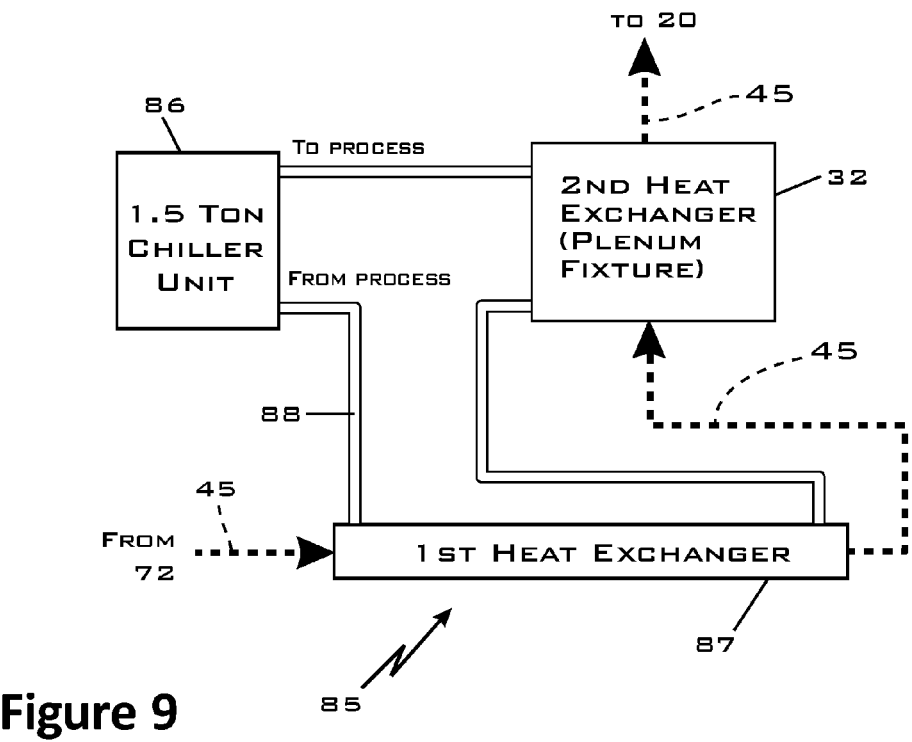
FIG. 9 is a schematic diagram of the exemplary embodiment of the chiller for embodiment of FIG. 7.

Referring to FIGS. 1, 7B, 9 and 13B, the control (200) sets a frame counter to zero (527). With the infrared camera (34) in position, the control (200) commands the infrared camera (34) to start capturing infrared images (530) at the needed sample rate (531), $t_s$ that is recalled from memory (213). After the sample rate has expired, the frame counter is incremented (532) and compared (528) with needed number of frames (526). If the frame counter is less than the needed number of frames, e.g., (528(y)), another infrared image is captured while the downstream heat flux (43, 44) is directed on the infrared camera's field of view. Each infrared image is stored in a fast memory device (213) for later recall. The memory device may be one of several commercially available solid state hard drives, for example a solid state hard drive commercially available from SAMSUNG Electronics Co. Ltd. of Korea. If the frame counter is not less than the number of frames (528(n)), signaling the needed length of time, $t_d$, the control (200) commands a gas supply valve (64) and diverter valve (62) to open in a position that allows coolant (45) from a source of pressurized helium (52) to flow into the third pressure regulator (72). The control (200) is electrically connected to a chiller (85) and a second temperature sensor (93) providing a second temperature feedback signal. Referring to FIG. 9, the chiller (85) comprises a one and half ton chiller unit (86), a first heat exchanger (87) of five hundred square inches of cooling area and a second heat exchanger (32) of twenty six square inches of cooling area. The chiller process coolant (88), inhibited propylene glycol, is coupled such that it circulates through the chiller unit and heat exchangers. Referring to FIGS. 1 and 7B, the control (200) uses the second temperature feedback signal and a known PID algorithm in the control to operate the chiller and by convection to bring the coolant temperature, $T_u$, to a range of 10 to 70 degrees Fahrenheit. The value used is determined in the later described setup procedure. The control (200) also commands the third pressure regulator (72) to set the upstream gauge pressure, $P_u$, measured by the upstream pressure sensor (92) to the needed pressure ratio, $PR_u$, computed as denoted by equation 15 using the measurement of $P_a$ sensor and $PR_u$ in the range of 1.1 to 3.0. The value used is determined in the later described setup procedure. The upstream pressure sensor (92) provides the third pressure feedback signal. The control (200) uses the third pressure sensor feedback signal and a known PID algorithm in the control to set $P_u$. At the moment of time $t_d$ expires, the control (200) operates the coolant valve (65) allowing the coolant (45) to rapidly flow into the plenum fixture (32). This coolant valve may be one of several commercially available rapid acting solenoid valves, for example an ASCO® RedHat 8210G from ASCO of Florham Park, N.J. When this coolant is rapidly discharged (e.g., setting the upstream conditions at block 537) onto the blade's hotter outer skin (16) it generates an isolated cooling effect (40) to radiate near the film cooling feature, as best shown in FIG. 3. Again, the control computes the needed number of frames (at block 533) and sets the frame counter to zero (at block 534). The control (200) commands the infrared camera (34) to capture an infrared image (at block 538) and the needed sample rate is allowed to expire (at block 539). The control (200) then increments the frame counter (at block 540) and compares it with the number of frames (at block 535). If the frame counter is less than the number of frames (535(y)), another infrared image is captured and stored in memory (213) while the coolant is allowed to flow through the plenum fixture, the flow fixture (20), the seal (24), the opening (7) at the base (19) of the blade (10), the internal cavity (8) of the blade (10) and to discharge through the plurality of cooling features (12) that are being inspected. The infrared camera (34) continues to capture infrared images at $t_s$ that are stored in memory (213). The needed $T_u$, $PR_u$, $t_d$, $t_u$, and $t_s$ settings were previously stored in the network database (300) for each position (521), shown in FIG. 13B, and is recalled by the control (200) as needed by the inspection cycle program (211).

$$P_u = (PR_u - 1) \times P_a \qquad \text{Equation 15}$$

Referring to FIGS. 3, 7B, 13B and 14, if the frame counter is not less than the number of frames (535(n)), signaling the needed upstream dwell time, $t_u$, has expired, the controller (200) commands the coolant valve (65) to turn off (536) and the infrared camera (34) to stop capturing images. The control increments the position counter (541) and compares (520) it with the number of needed positions. If the position counter is less than the number of positions, the infrared camera (34) is moved to the next position as provided by the blade inspection procedure (504). With respect to FIG. 13B, once in position, the previously described, relative individual cooling effect data acquisition method is repeated, until the cooling effect (40) of every cooling feature (12) has been captured by the infrared camera (34). With the cooling effect (40) of every cooling feature (12) captured, the downstream heat flux is turned off (542) and the relative individual cooling effect identification method (700) is processed.

In a second exemplary embodiment of the relative individual cooling effect data acquisition method, the coolant (45) is a mixture of helium and air.

Figure 14:
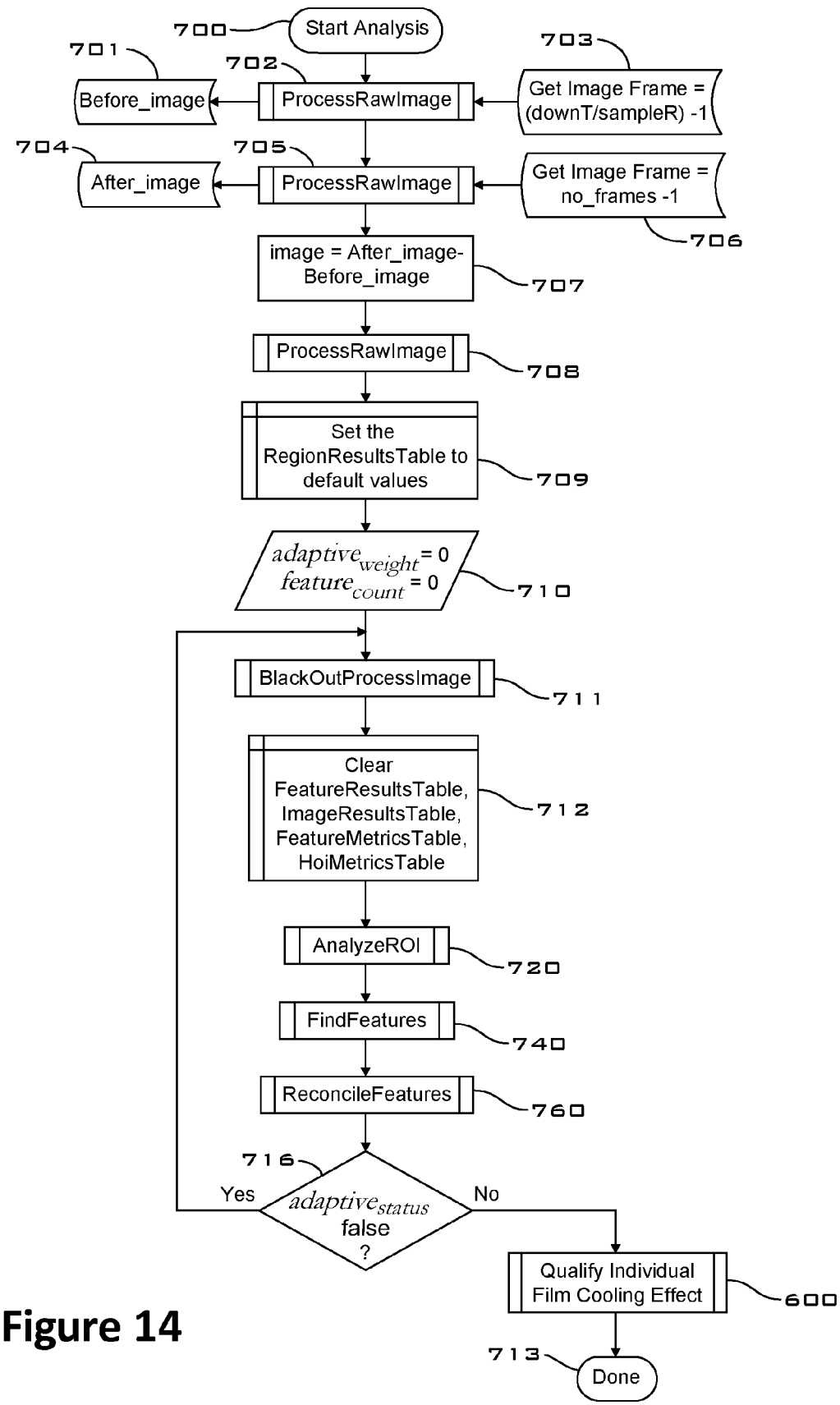
FIG. 14 is an overall flow chart of an exemplary embodiment of the method for analyzing infrared images used to detect and quantify the film cooling effect generated by a film cooling feature for the embodiment of the FIGS. 13A and 13B method.

Referring to FIGS. 7B and 14, in one exemplary embodiment of the relative individual cooling effect identification method (700), the control (200) recalls (702) from memory (213) the infrared image for the last position captured at the end (703) of $t_d$, named the "b" frame (701). The frame comprises a two dimensional array of temperatures, where a single temperature is named a "pixel". Then the control recalls (705) from memory the frame for the last image captured at the end (706) of $t_u$, named the "a" frame (704). The control creates a difference array of the "b" and "a" frames in a process as claimed in U.S. Pat. No. 7,791,025. This difference array (707) is denoted $I_f$ and named the "raw image". The descriptive statistics for array $I_f$ are computed by the controller. Both the array $I_f$ and descriptive statistics is stored in the memory (212). The control continues processing (708, 709) the raw image into a color image (708a, see FIGS. 22, 23 and 24), where all records in various tables are deleted (712) prior to further proceedings.

Figure 22:
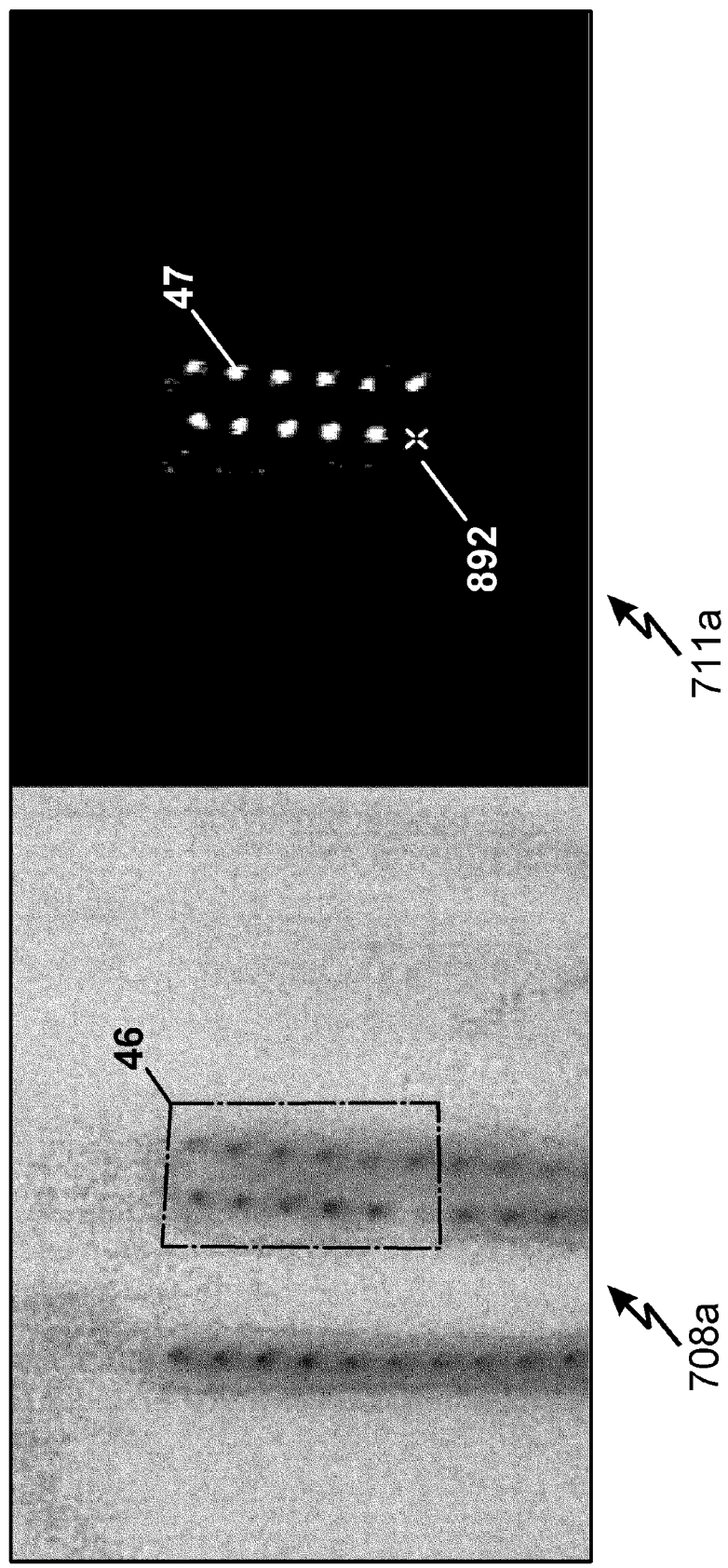
FIG. 22 is an example of raw and processed images for a group of pressure holes rendered in accordance with the principles of the present invention. A known defect is identified with an "X".
Figure 23:
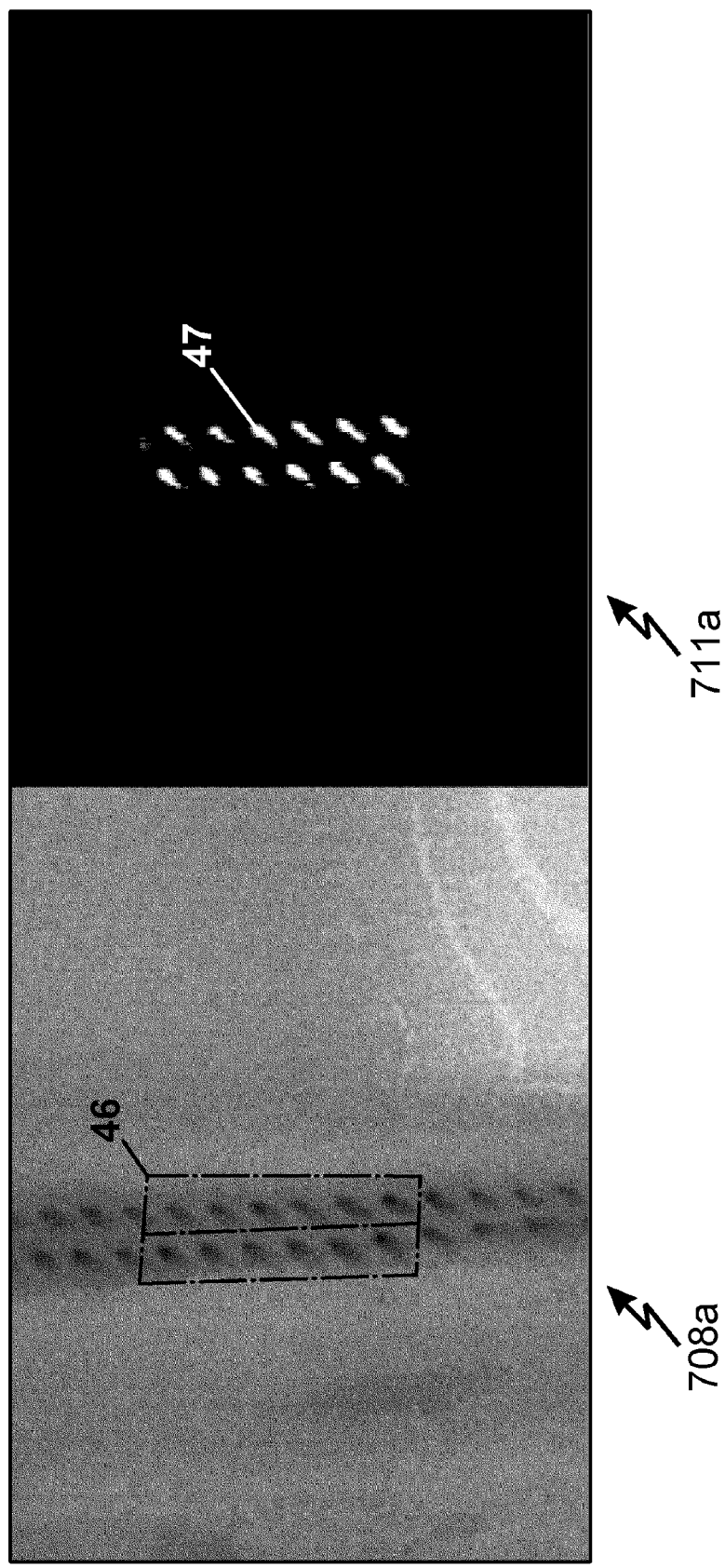
FIG. 23 is an example of raw and processed images for a group of suction holes rendered in accordance with the principles of the present invention.
Figure 24:
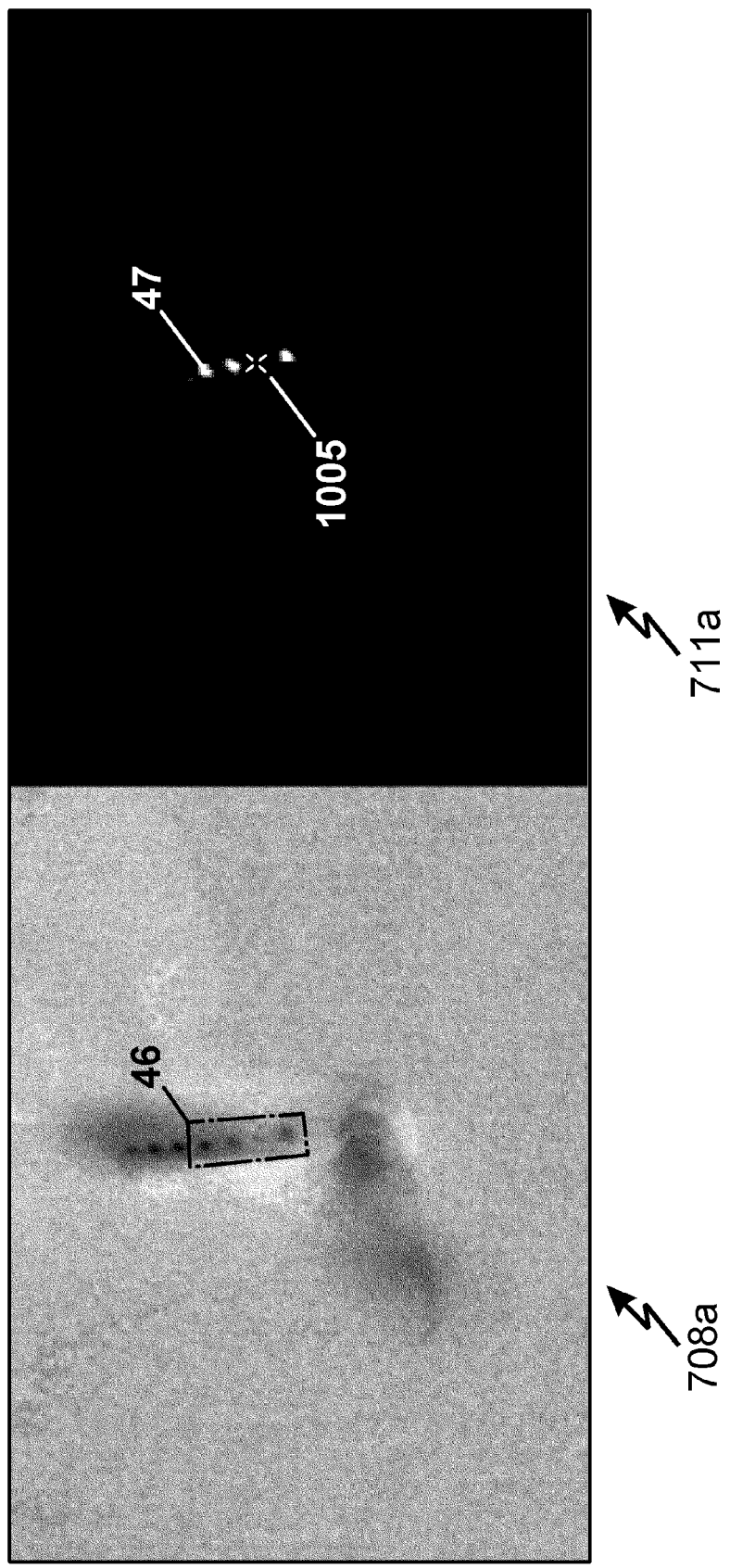
FIG. 24 is an example of raw and process images for a group of showerhead holes rendered in accordance with the principles of the present invention. A known defect is identified with an "X".

Referring to FIGS. 7B and 14, the control (200) renders on the monitor (221) the raw image as pseudo color image (708a) by processing a look-up-table containing 120 unique colors, best illustrated in FIGS. 22, 23 and 24. Each color represents a subgroup of temperatures found in the raw image. The $color_{index}$ is computed by the control as denoted by equation 16 where $b_0$ and $b_1$ is statistically determined from a least square model of the maximum and minimum temperatures recalled from the $I_f$ descriptive statistics stored in memory (212). A copy of the rendered raw image is stored in memory (213, 543) for later recall.

$$Color_{index} = temperature \times b_1 + b_0 \qquad \text{Equation 16}$$

Figure 16:
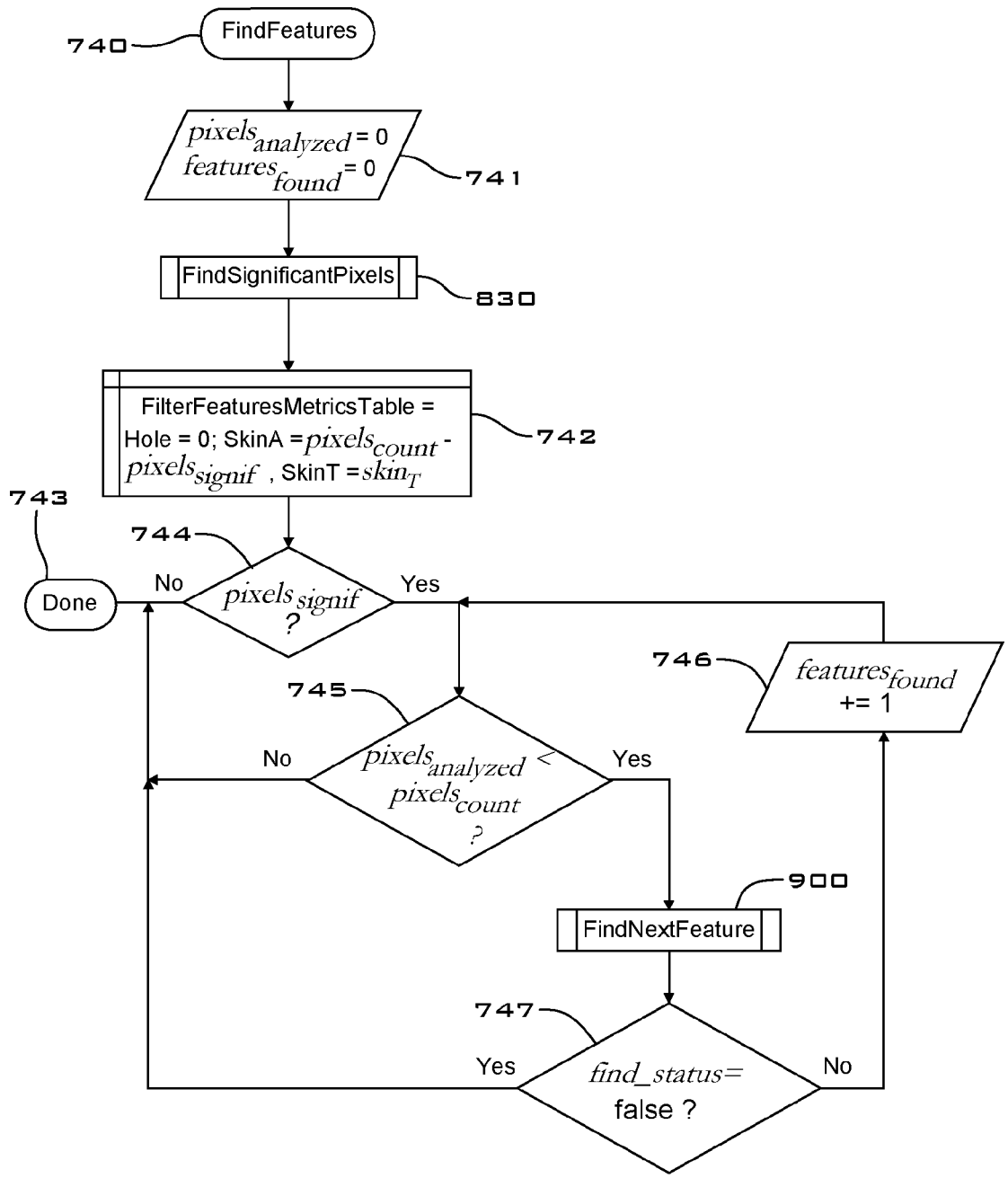
FIG. 16 is a flow chart for the method used to identifying a film cooling effect within a region of interest for the embodiment of the FIG. 14 method.

Referring to FIGS. 22, 23 and 24, a Region-of-Interest "ROI" (46) defines the boundaries of pixels around where a collection of film cooling effects is expected to be within the array $I_f$. The ROI is defined by a quadrilateral having end point coordinates of $x_0$, $y_0$ and $x_1$, $y_1$ and $x_2$, $y_2$ and $x_3$, $y_3$ which describe the top left hand, top right hand, bottom right hand and bottom left hand end points. These end points are established during the setup procedure and stored in the network database (300), see FIG. 7B. Referring to FIGS. 7B, 15 and 16, the exemplary embodiment of the ROI analysis method (720), control (200) is processed to identify pixels that have a large statistical temperature difference. First a sub-array, $I_r$, of array $I_f$ is located by finding the extreme boundary of points that are inclusive of the ROI (at block 820). The descriptive statistics for the $I_r$ array is computed at block (825). These statistics are stored in memory (212). A factor denoted $k_{factor}$ is then computed (at block 721) as denoted by equation 17, where the $adaptive_{weight}$ is initially set to zero (710) and constants $k_A$, $k_B$ and $k_C$ are determined empirically during the setup procedure. The control continues processing the ROI analysis method, such as by inserting the appropriate feature metrics table record (at block 723), inserting the appropriate region results table record (at block 724), and ending the ROI analysis when done (at block 725), as shown in detail in FIG. 15.

$$k_{factor} = k_A \times ROI_{min}^2 - k_B \times ROI_{min} + k_C + adpative_{weight} \qquad \text{Equation 17}$$

Referring to FIGS. 1, 3, 7B and 15, the control (200) continues processing the ROI analysis method to compute a pixel threshold or "frame threshold" (at block 722), labeled ROI threshold, as denoted by equation 18. This threshold represents the temperature limit at which a pixel is either classified as "significant", probably a fragment of a film cooling effect (40), or a portion of the skin of the blade (16). The term $ROI_{area}$ is the total count of pixels inside the ROI (46), best shown in FIGS. 22, 23 and 24. The natural logarithm of $ROI_{area}$ is used in this computation.

$$ROI_{threshold} = \sqrt{k_{factor} \times ROI_{stdev} \times \log(ROI_{area})} + ROI_{min} \qquad \text{Equation 18}$$

Figure 17:
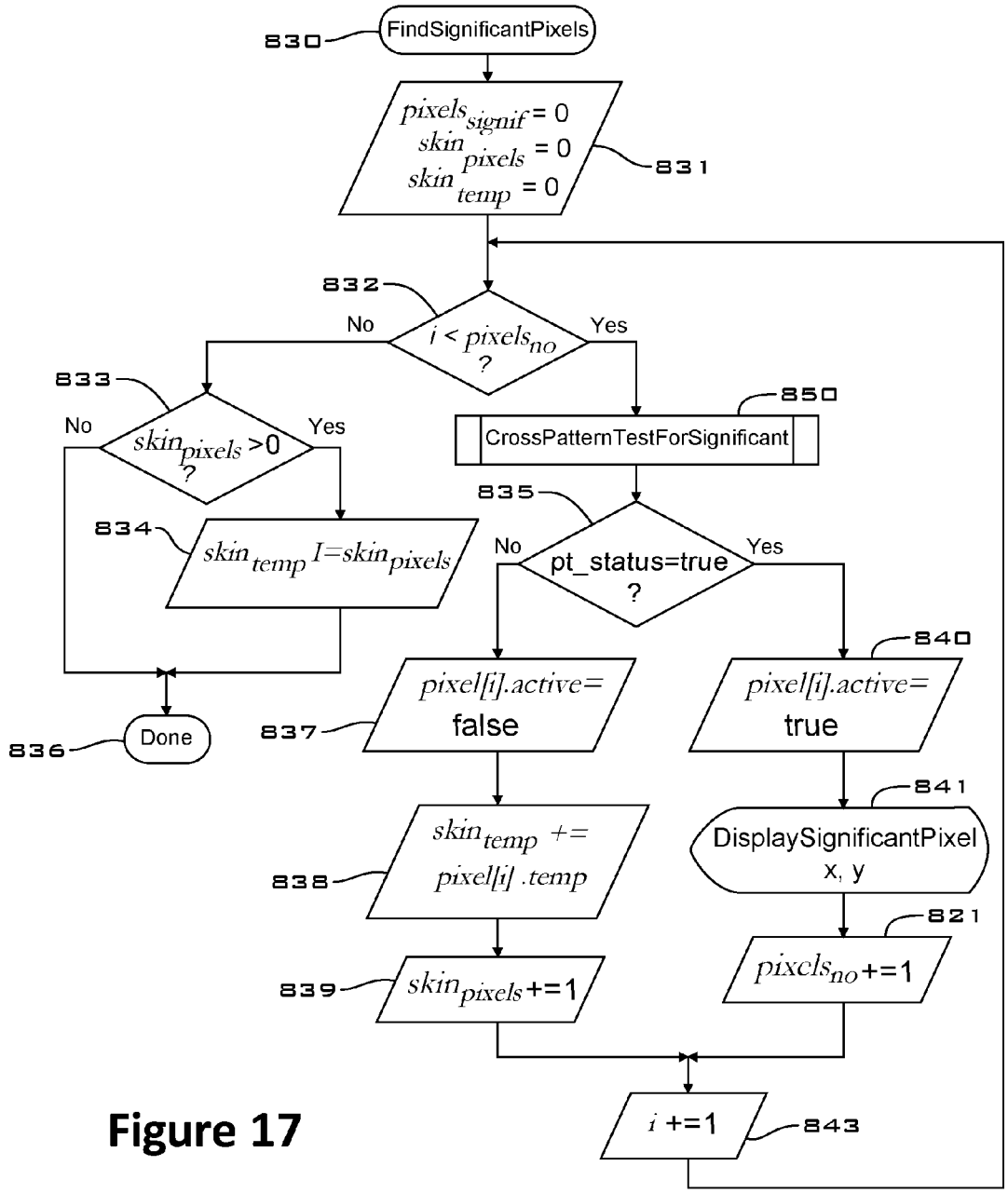
FIG. 17 is a flow chart of an exemplary embodiment of the method for identifying significant pixels in the region of interest by the embodiment for the FIG. 16 method.
Figure 18A:
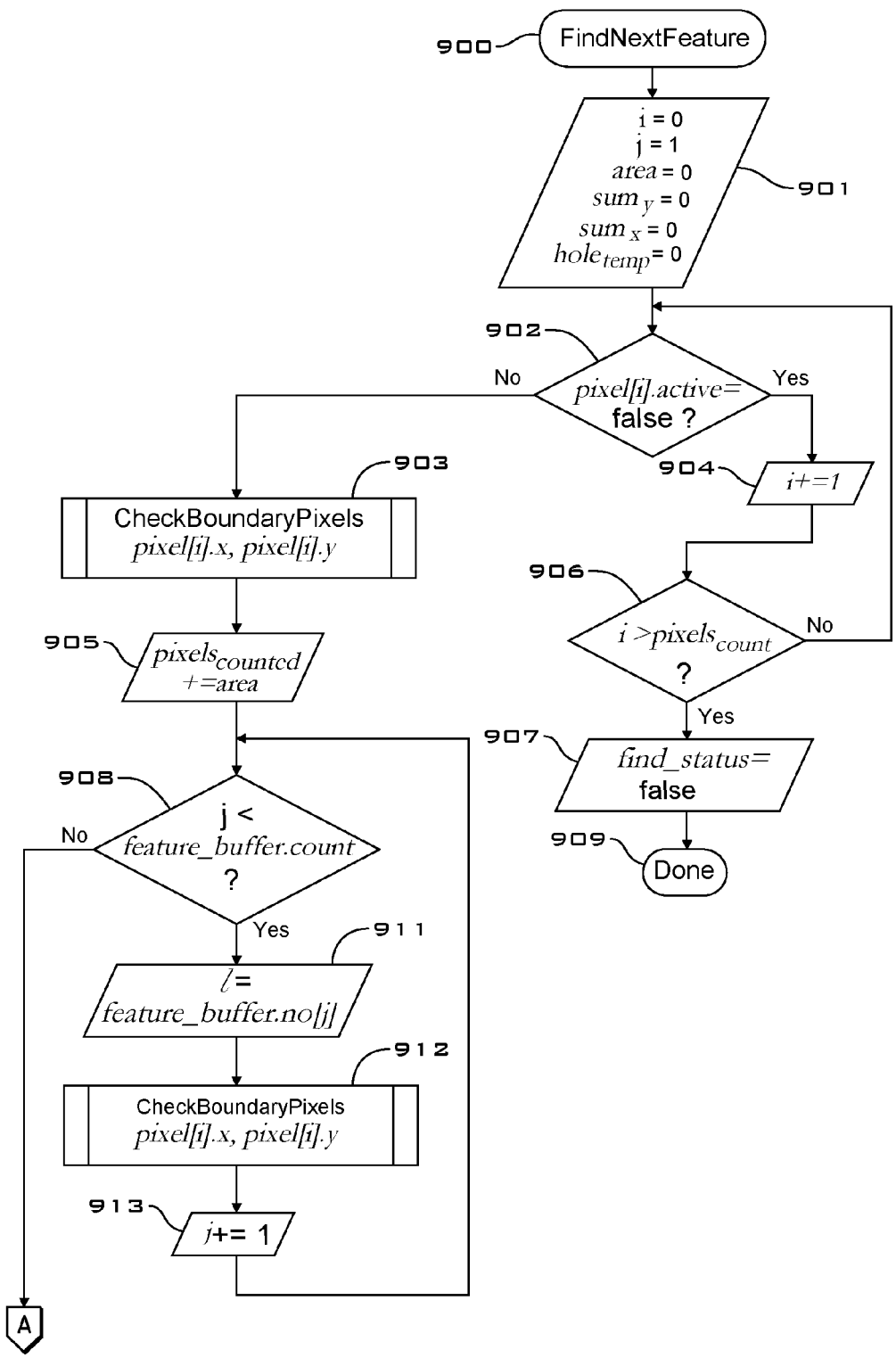
FIG. 18A is a flow chart of the film cooling effect, feature and identification method for the embodiment of the FIG. 16 method as continued in FIG. 18B.

Referring to FIGS. 1, 7, 14, 16, 17, 18A, 18B and 22, the control (200) continues processing pixels within the ROI (46) by identifying all significant pixels in the $I_r$ array and grouping these pixels into possible cooling effect features (12). First the control (200) sets a pixels analyzed counter and features found count to zero (741). Each pixel in the $I_r$ array is tested by comparison with the ROI threshold. This significant point detection process (830, 831-843 and 850) is as claimed in U.S. Pat. No. 7,791,025. If no significant pixels are found (744), the control aborts further processing (743). Conversely, at step (744) the spatial X-Y coordinates for pixels identified as significant are stored in a memory (212). Once all of the significant pixels have been identified the control (200) starts processing the feature identification process (900, 901), comprising a main loop (including blocks 745, 746, 747, 900 as shown in FIG. 16). As shown in FIG. 18A, this identification process (900, 901) comprises a first loop (including blocks 902, 904, 906, 907, 909) where each pixel within the ROI identified as significant is grouped by an eight-cell boundary test (912), also as claimed in U.S. Pat. No. 7,791,025. This test in FIG. 18A also comprises a second loop (including blocks 903, 905, 908, 911, 912, 913) that groups significant pixels that border other significant pixels into what is named an "array of probable individual film cooling effects". This identification and grouping process continues until every pixel in the $I_r$ array has been processed. This array of probable individual film cooling effects is then stored in memory (212). A third loop (including blocks 910, 914, 916, 919, 924, 925 in FIG. 18B) iterates each of the pixels that have been grouped together computing statistics needed to for further processing. The control continues processing (by following the blocks 915, 917, 920, 923, 926, 927, 928, 930 in FIG. 18B) updating various tables and computing the count of significant pixels, named "area", for each probable effect and its centroid, denoted $x_p$ and $y_p$ and storing them in memory. With all of the significant pixels grouped and statistics computed (931) the feature reconciliation process begins (760).

Referring to FIGS. 1, 3, 7B, 14, 18A, 18B, 19A and 19B, the control (200) continues processing (760, 761, 762, 763) each probable effect by reconciling its $x_p$ and $y_p$ coordinate with each expected cooling effect target coordinate within the ROI (46) as recalled from the network database (300). If no probable effects were identified (900) a new $ROI_{threshold}$ is computed (764, 765) and the feature reconciliation process is aborted (766) as described in further detail. If a feature cannot be reconciled for an expected feature (918,921), the feature area is set to zero and the reconciliation process proceeds with the next expected feature. To account for normal fabrication variances, a predefined positional tolerance is added to and subtracted from the target coordinate and used for this comparison process. The target coordinate and tolerances are determined by the setup procedure. The control processes a fourth loop (767-774) and a fifth loop (775-784) such that when the center point of a probable effect matches that of a target center point, the characteristics for it are recalled from memory (212) and stored in a database table named the "reconciled effects table". These characteristics include the design name of cooling feature (12) that generated the effect (40), its area denoted $A_i$, and its $x_p$ and $y_p$ coordinate. This identification process continues until all probable effects have been reconciled (768) by the control. If all probable effects have been processed and a target center point is not reconciled by the control, then an effects table record is inserted with an $A_i$, of zero. If the count of reconciled effects is less than one, then the $ROI_{threshold}$ is modified as herein described and then the control repeats the ROI analysis method (720) process using the new $ROI_{threshold}$.

Referring to FIGS. 1, 7B, 19C, 19D, 20 and 22, in the relative individual cooling effect identification method the control (200) further continues processing (at the series of blocks 785-803, 805, 860, 809, 812, 850, 806, 808, 880, 807, 811, 810, 807, 811, 810, 813) to determine whether the reconciled effects are statistically probable. A proportion, p, of the summation of the reconciled effect area and ROI area is computed and stored in memory. An $adaptive_{minor\_limit}$ and $adaptive_{blob\_limit}$ is then computed as denoted by equations 19 and 20, using the reconciled effect areas and ROI area stored in memory. The term $expected_{count}$ is the quantity of cooling features expected by design and located within the ROI (46). The term $expected_{area}$ is the area, in units of square inch, of the effected cooling surface, $A_e$, on the skin (16) of the blade (10), times 10,000. The use of the $expected_{area}$ compensates for differences in the size of showerhead (11), pressure (15), suction (13) and tip (14) holes. For simple cooling features (12), such as holes, this area is the area of hole. For complex cooling features, such as a shaped hole, this area is computed from the perimeter of the shape on the outer surface of the airfoil using known methods. The natural logarithm of $expected_{area}$ is used in computation of equations 19 and 20.

$$adaptive_{blob\_limit} = \frac{expected_{count} \times \log(expected_{area}) \times 20}{ROI_{area}}$$ Equation 19

$$adaptive_{minor\_limit} = \frac{expected_{count} \times \log(expected_{area}) \times 10}{ROI_{area}}$$ Equation 20

Figure 20:
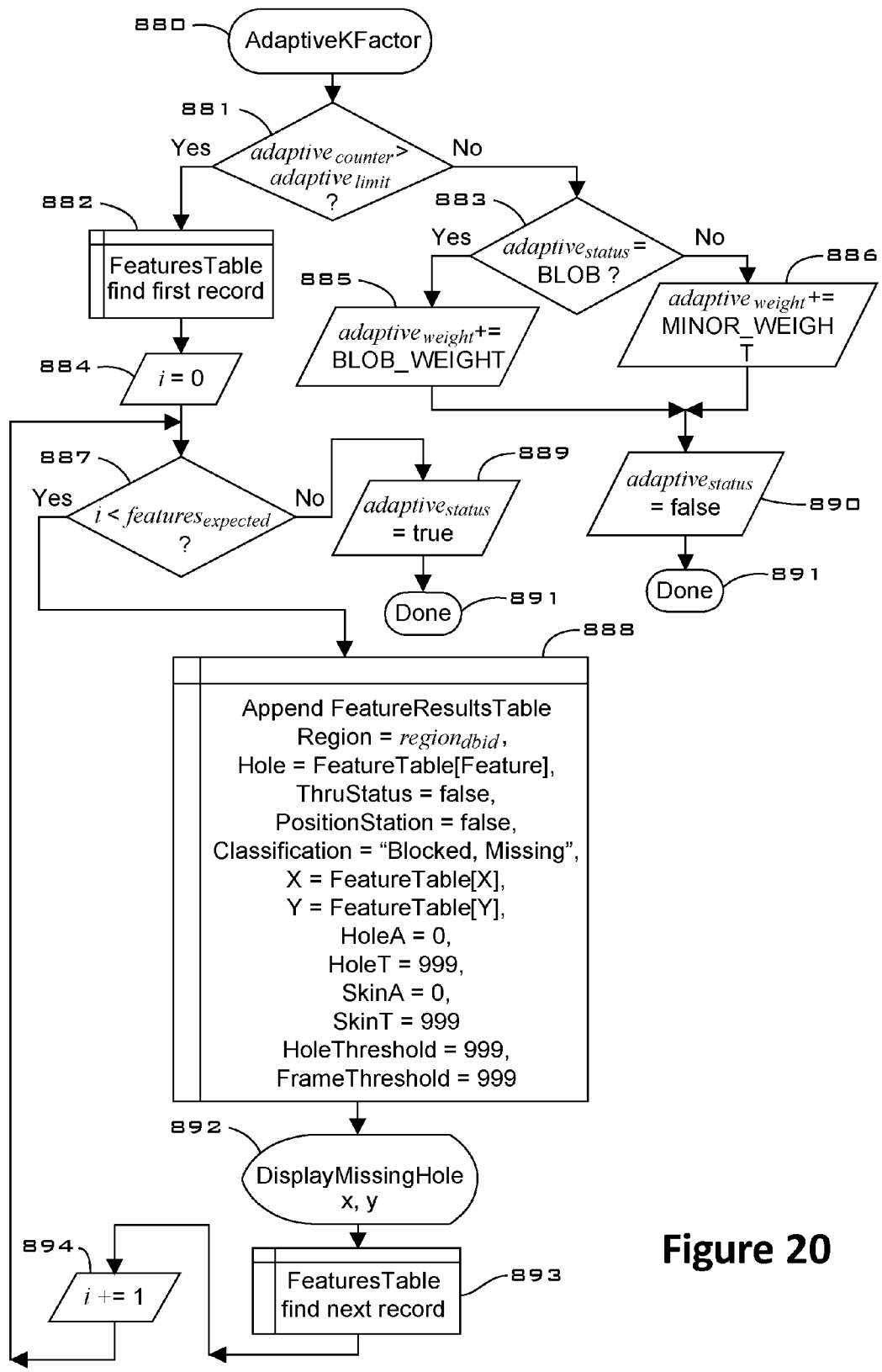
FIG. 20 is a flow chart of an exemplary embodiment of the method for adaptively computing the significant pixel threshold for the embodiment of the FIG. 19 method.

Referring to FIGS. 7B, 14 and 20 at block 716, if p is greater than the $adaptive_{blob\_limit}$, which is one of the conditions shown as (716(y)) in FIG. 14, then the $ROI_{threshold}$ is modified and the control (200) repeats the ROI analysis (720) process using the new $ROI_{threshold}$ If p is less than the $adaptive_{minor\_limit}$, which is another of the conditions shown as (716(y)) in FIG. 14, then the $ROI_{threshold}$ is modified and then the control repeats the ROI analysis (720) process using the new $ROI_{threshold}$. If neither of these two conditions is true, which is the condition shown as (716(n)) in FIG. 14, then the reconciled effects are further processed by the relative individual cooling effect classification methods (such as at block 860 shown in detail at FIG. 21) herein described.

Referring to FIGS. 7B and 20, when the $ROI_{threshold}$ term is needed to be modified (at the series of blocks 880-894), the $k_{factor}$ is changed by either increasing or decreasing its value by adding or subtracting a newly computed $adaptive_{weight}$. When p is greater than the $adaptive_{blob\_limit}$, the value of the $adaptive_{weight}$ is changed by adding a predefined amount of the $blob_{weight}$. When p is less than the $adaptive_{minor\_limit}$, the value of the $adaptive_{weight}$ is changed by subtracting a predefined amount of the $minor_{weight}$. The value of constants $blob_{weight}$ and $minor_{weight}$ are determined empirically during the setup procedure and stored in the network database (300). Using the value of new $adaptive_{weight}$ the $ROI_{threshold}$ is computed as denoted by equation 17 and the complete ROI analysis process (including blocks 711, 712, 720, 740, 760, 716) is repeated.

Figure 19A:
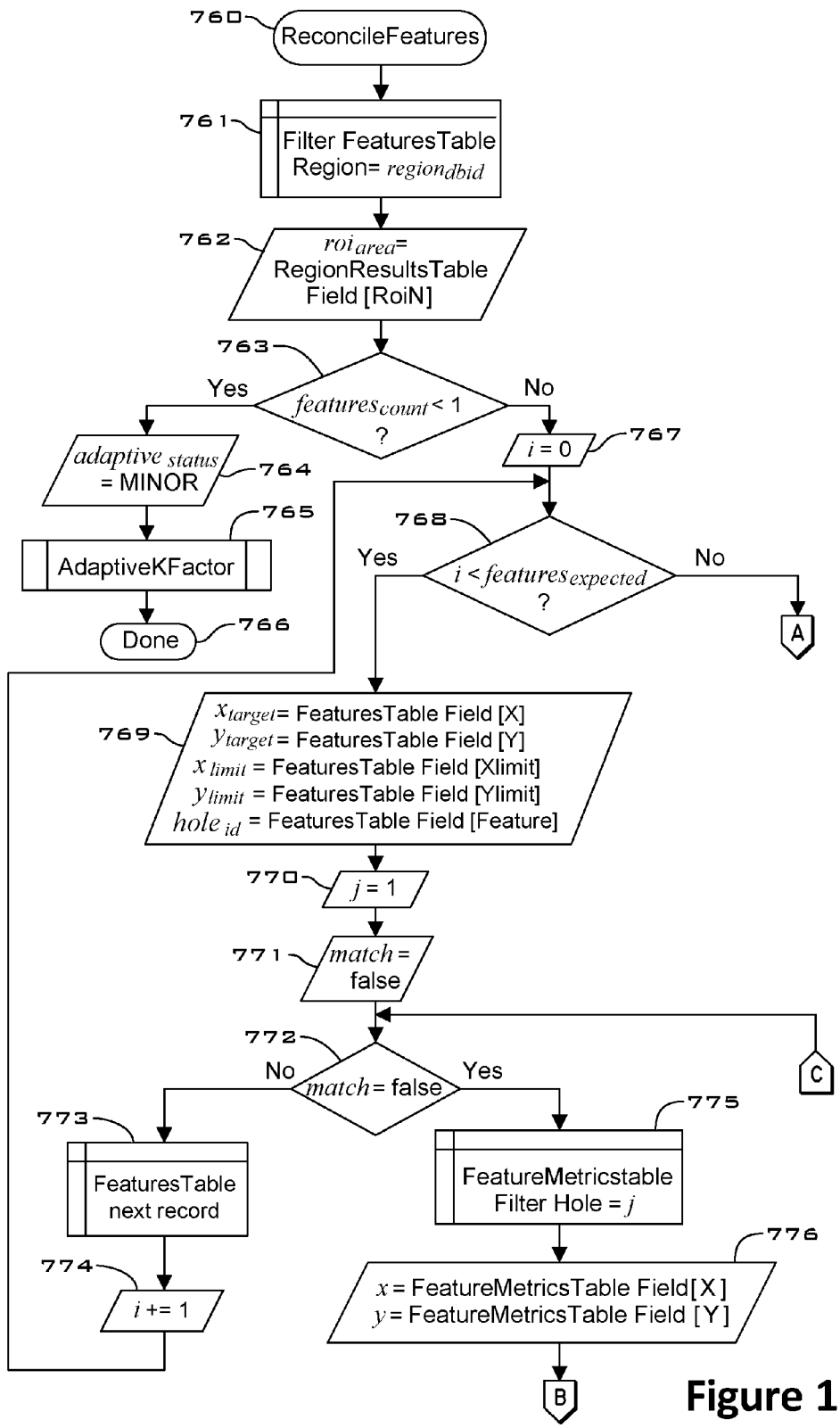
FIG. 19A is a portion of a flow chart of an exemplary embodiment of the method for reconciling identified cooling effects with the expected location of the cooling effect for the embodiment of the FIG. 14 method.
Figure 19B:
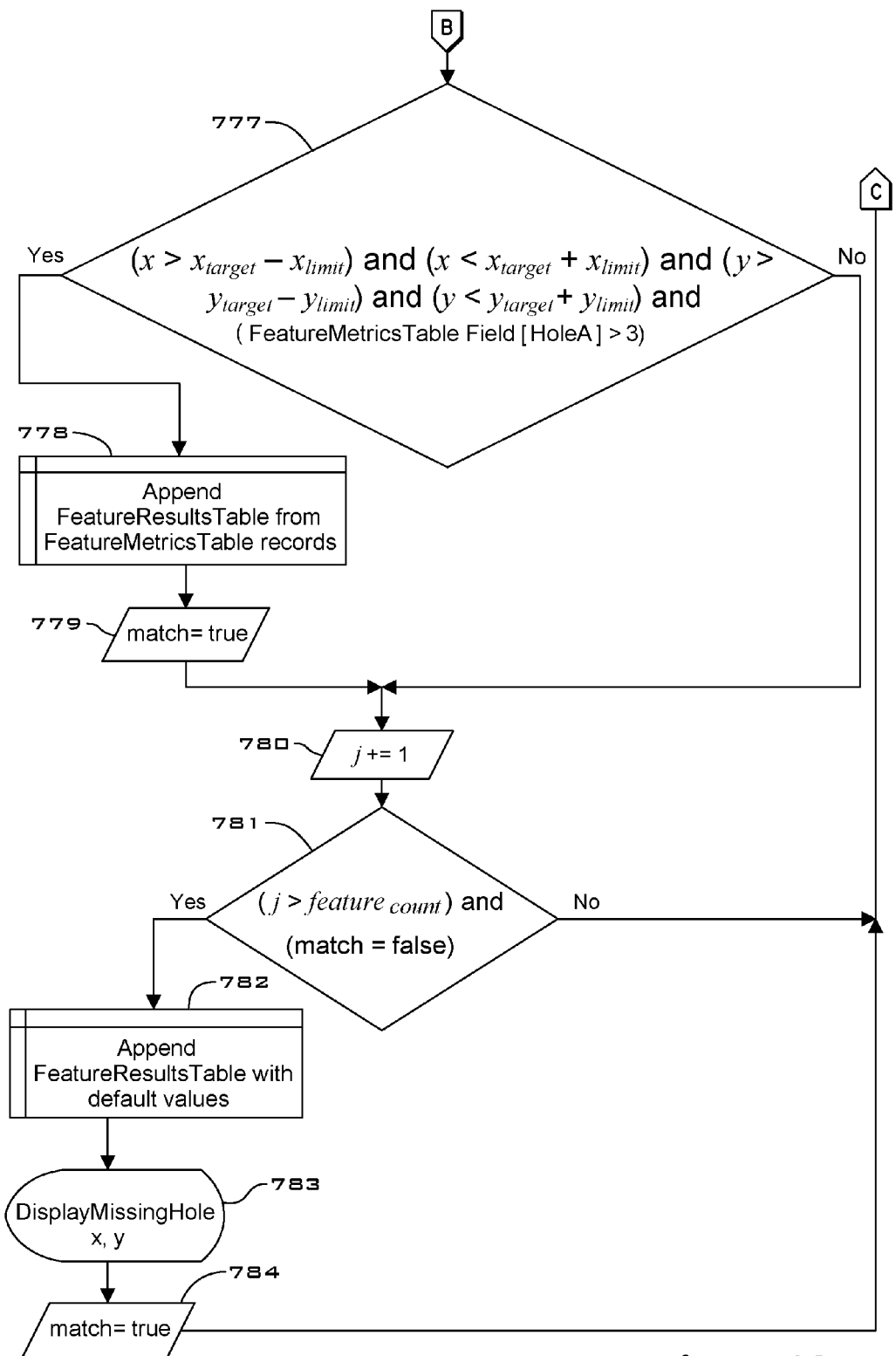
FIG. 19B is a portion of a flow chart of an exemplary embodiment of the method for reconciling identified cooling effects with the expected location of the cooling effect for the embodiment of the FIG. 14 method.
Figure 19C:
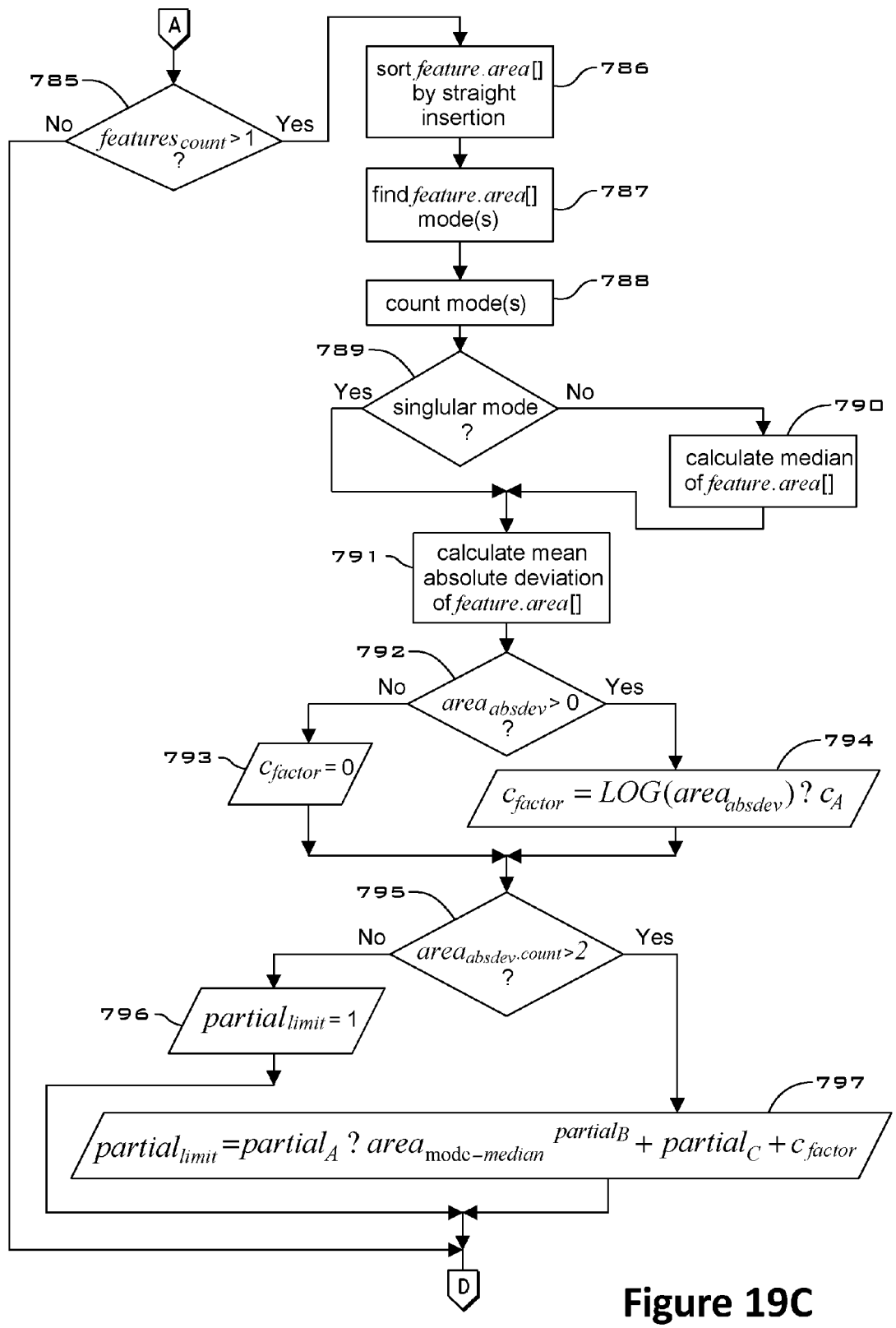
FIG. 19C is a portion of a flow chart of an exemplary embodiment of the method for reconciling identified cooling effects with the expected location of the cooling effect for the embodiment of the FIG. 14 method.
Figure 19D:
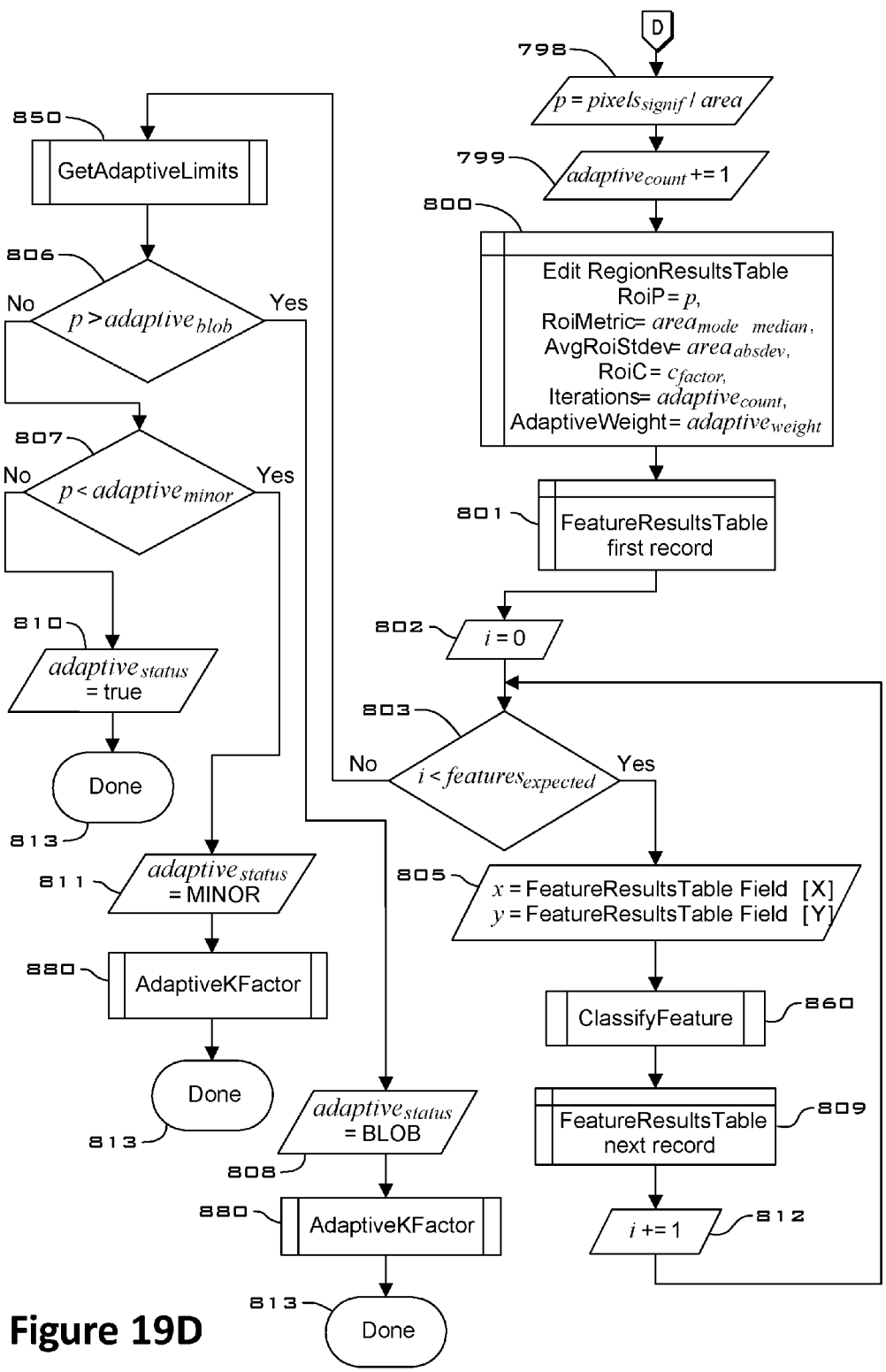
FIG. 19D is a portion of a flow chart of an exemplary embodiment of the method for reconciling identified cooling effects with the expected location of the cooling effect for the embodiment of the FIG. 14 method.
Figure 21:
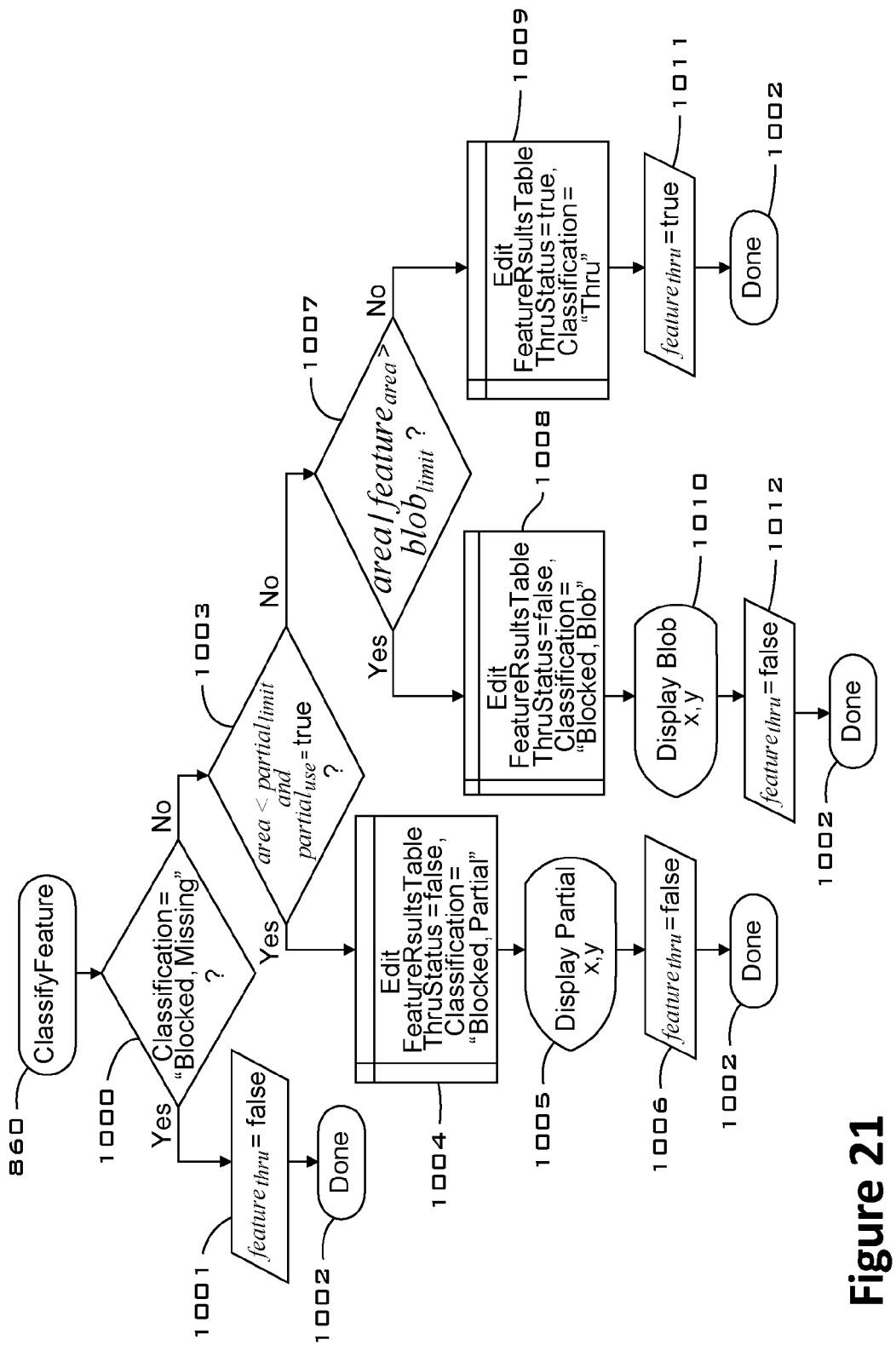
FIG. 21 is a flow chart of the embodiment of the method of classifying the film cooling effect for the embodiment of the FIG. 14 method.

Referring to FIGS. 7B, 19D and 21, the exemplary embodiment of the relative individual cooling effect classification method (including series of blocks 860 and 1000-1012) the control (200) computes a set of statistical limits that each reconciled effect is compared with. The partial limit defines the minimum area a reconciled effect must exceed to be considered a true cooling effect. A reconciled effect with an area less than the partial limit is classified "missing" and its area, $A_i$, set to zero. The control computes the partial limit (797), denoted $partial_{limit}$, using the herein described method. First the reconciled effects are ordered by the size of their area using a known straight insertion algorithm (786). Then the mode or modes of the ordered areas is solved (787). If there is no singular mode then the median of the reconciled effect areas is determined. Using the value of the either mode or median area, $mean_{mode}$, the mean absolute deviation, $mean_{abs\_dev}$, is computed (791). A sensitivity factor, denoted $c_{factor}$ is computed as denoted by equation 21. The constant $c_A$ is determined empirically during the setup procedure and stored in the network database (300). Next the $partial_{limit}$ is computed as denoted by equation 22. Constants $p_A$, $p_B$, and $p_C$ are determined empirically during the setup procedure and stored in the network database. A blob limit, denoted $blob_{limit}$, defines the maximum size a reconciled effect can be a considered a true cooling effect. The $blob_{limit}$ is established during the setup procedure and stored in the network database (300). A reconciled effect with an area greater than the $blob_{limit}$ is classified "missing" and its area, $A_i$, set to zero.

$$c_{factor} = \log(mean_{abs\_dev}) \times c_A$$ Equation 21

$$partial_{limit} = p_A \times mean_{mode}^{p_B} + p_c + c_{factor}$$ Equation 22

Referring to FIGS. 7A and 14, to perform a black out process (711), the control (200) initializes a binary type processed image array, the same dimensions as $I_r$, in memory (212). This processed image array is denoted $I_p$. Each element of $I_p$ can either be zero or one. Initially all $I_p$ elements are set to zero, which visually symbolizes a black process image. Recalling each of the significant pixels for the plurality of reconciled effects that have an area greater than zero, the $I_p$ element is set to one. Once the control has completed this black out process (711), the array is rendered on the monitor (221) on a black background, changing the color to white (47)

when the $I_p$ element is one, refer to the image (711*a*) on FIGS. 22, 23 and 24. The color white visually symbolizes an element of the individual film cooling effect (47). A copy of the rendered processed image is stored in memory (213, 543) for later recall.

Referring to FIGS. 14 and 23, in a second exemplary embodiment of the relative individual cooling effect identification method, a raw image may contain more than one ROI (46), whereby the next ROI is processed by the previously described ROI analysis method (including blocks 711, 712, 720, 740, 760, 716) ending the analysis method (713).

Referring to FIGS. 1, 7B and 13B, with the infrared inspection completed, the control (200) commands the flow fixture (20) to release (544) the blade (10), the robot arm (33) to return to its home position (545) and the inspector to remove (546) the blade from the flow fixture (20). The inspector can then inspect another blade or exit the inspection cycle program (547).

Referring to FIGS. 1, 7 and 14, with every reconciled effect classified (713) by the control (200), the control starts the absolute individual film cooling effect quantification method (600) by computing the total cooling effect area, denoted $A_t$, as denoted by equation 23, where expected$_{count}$ is number of expected cooling effects. Next the control creates another new floating point array in memory (212) the size of expected$_{count}$. This array is labeled the proportional cooling effect area, $\rho_i$, where $i$ is the identification number assigned to cooling feature during the setup procedure. $\rho_i$ is computed for each corresponding $A_i$, as denoted by equations 24 or 25, where $c_i$ is a correction factor to compensate for errors caused by differences in the coolant (45) pressure ratio used during the infrared imaging. For example, it is known that showerhead features do not thermally respond the same as suction (13) features or pressure (15) features. To compensate for this fact, the coolant pressure ratio is changed for the different cooling features. This causes a bias that needs to be taken into account. The $c_i$ computed as denoted by equation 26 or is determined empirically during the setup procedure.

$$A_t = \sum_{i=1}^{expected_{count}} A_i \qquad \text{Equation 23}$$

$$A_i 0 \to \rho_i = 0 \qquad \text{Equation 24}$$

$$A_i > 0 \to \rho_i = \frac{A_i \times c_i}{A_t} \qquad \text{Equation 25}$$

$$c_i = \sqrt{\frac{PR_u - 1}{PR_r - 1}} \qquad \text{Equation 26}$$

Referring to FIGS. 1, 3 and 7B, finally, the film cooling effect (40), denoted $E_i$, for each film cooling feature (12) is computed as a proportion of the total mass rate of airflow $m_t$ by the control (200) as denoted by equation 27, where $i$ is the identification number assigned to cooling feature during the setup procedure. The value of $E_i$ is stored in the network database (300) for later recall. The $E_i$ is then compared with design limits of the cooling feature inspected and its quality status is determined to be conforming or nonconforming. In the case where no design limits exist, a sample of blades known to meet the film cooling effect design intent is inspected using the principles of this invention and limits statistically determined and stored in the network database. The quality status is stored in the network database and can be later recalled. For example the quality status can be recalled prior to releasing the blade for shipment to the customer, to ensure the blade (10) conforms to the design intent for film cooling effects generated by the fabricated film cooling features, thus eliminating the possibility of shipping a nonconforming blade.

$$E_i = \rho_i \times c_i \times m_t \qquad \text{Equation 27}$$

Referring to FIGS. 1 and 7B, the infrared inspection setup procedure processes a sample of blades (10) with known good and bad cooling features fabricated. This sample of blades is used in an experiment designed to determine the optimum settings for $T_d$, $PR_d$, $V_e$, $T_u$, $PR_u$, $t_d$, $t_u$, and $t_s$ to be used for each position and each group of cooling features (12). This process starts by either manually or with the use of a computer aided design program, the infrared camera (34) position coordinates x, y, z, rx, ry and rz are defined and stored in the network database (300). When the sufficient number of positions is defined to view all of the film cooling features (12), the designed experiment runs are executed. Each run varies the level of $T_d$, $PR_d$, $V_e$, $T_u$, $PR_u$, $t_d$, $t_u$, and L. With all needed runs completed, analysis of the data can be performed using known experimental methods, that can be aided by a commercial product like Minitab, Minitab Inc. of State College, Pa. The values for the optimum settings are stored in the network database. Values for constants $c_A$, $p_A$, $p_B$, $p_C$ and blob$_{limit}$ are similarly obtained by experimental methods and stored in the network database.

With respect to FIGS. 14 and 16, the Find Features method (740), which is part of the ROI analysis process described herein, first initializes block (741), the Find Significant Pixels method (830) is executed, variables in block (742) are initialized. If decision block (744) evaluates true (744(*y*)) and decision block (745) evaluates true (745(*y*)), the Find Next Features method (900) is executed, and if its result is tested at decision block (747) to be false (747(*y*)), the method (740) is done (at block 743). Conversely, if decision block (744) evaluates false (744(*n*)), the Find Features method (740) is done (at block 743). Conversely, if decision block 745 evaluates false (745(*n*)), the Find Features method (740) is done (at block 743). Conversely, if decision block 747 evaluates true (747(*n*)), features found are incremented (at block 746) and decision block 745 is repeated.

In regards to FIG. 17, the Find Significant Pixels method (830) first initializes block (831) and is followed by decision block (832). If block (832) evaluates true (832(*y*)) the Cross Pattern Test For Significant method (850) is executed and if decision block (835) evaluates true (835(*y*)), the active pixel array element is set (840), the significant pixel symbol is displayed (841), pixel number is incremented (821), "i" is incremented (843) and block (832) is repeated. Conversely, if block (835) evaluates false (835(*n*)), the active pixel array element is set (837), skin temperature is summed (838), skin pixels are incremented (839), "i" is incremented (at block 843) and block (832) is repeated. Conversely, if block (832) evaluates false (832(*n*)) and decision block (833) evaluates false (833(*n*)) the Find Significant Pixels method (830) is done (at block 836). Conversely, if decision block 833 evaluates true (833(*y*)), the skin temperature is set (at block 834) and the Find Significant Pixels method (830) is done at block (836).

With respect to FIGS. 19A, 19B, 19C and 19D, the Reconcile Features method (760) first filters the features table (761), the ROI area is set (762) and if block (763) evaluates true (763(*y*)) the adaptive status variable is set (764), the Adaptive K Factor method (765) is executed and algorithm (760) is done (766). Conversely, if block (763) evaluates false (763(*n*)), "i" is initialized (767) and if block (768) evaluates true (768(*y*)) various feature variables are initialized (769), "j" is initialized (770) and match is set (771). If block (772) evaluates false (772(*n*)) the features table is queried (773), "i" incremented (774) and the decision block (768) is repeated. Conversely, if block (772) evaluates true (772(*y*)) the feature metrics stable table is filtered (775), the coordinates for holes are set (776) followed by decision block (777). If the block (777) evaluates true (777(*y*)) the features results table is appended (778), match is set true (779) and "j" is incremented (780). Conversely, if block (777) evaluates false (777(*n*)) "j" is incremented (780). Decision block (781) follows block (780). If decision block (781) evaluates true (781(*y*)) the features results table is appended (782), a missing hole symbol is displayed at coordinates (783), match is set true (784) and block (772) is repeated. Conversely, if block (781) evaluates false (781(*n*)) block (772) is repeated. If block (768) evaluates false (768(*n*)), decision block (785) is evaluated. If block (785) evaluates true (785(*y*)), the feature areas is sorted (786), any modes found (787) and counted (788). If there is no singular mode (789(*n*)) the median of the feature areas is computed (790) and the mean absolute deviation is calculated (791). Conversely, if a single mode is found (789(*y*)) processing skips to block 791. Decision block (792) follows block (791). If block (792) evaluates true (792(*y*)) the c factor is computed (794). Conversely, if block (792) evaluates false (792(*n*)) the c factor is set (793). Following assignment of the c factor and if decision block (795) evaluates true (795(*y*)), the partial limit is computed (at block 797) and block (798) is executed. Conversely, if decision block 795 evaluates false (795(*n*)), the partial limit is set to be 1 at block (796) and block (798) is executed. Conversely, if decision block (785) evaluates false (785(*n*)), block (798) is executed. Variable "p" is computed (798), the adaptive count is incremented (799), the region results table is edited (800), features results table is set to the first record (801), "i" is set to zero at block (802), followed by decision block (803). If decision block (803) evaluates true (803(*y*)), the coordinates are set using the Feature Results Table fields at block (805), the Classify Feature method (at block 860) is performed, the next feature results table record is queried (at block 809), "i" is incremented (at block 812) and decision block (803) is evaluated again. Conversely, if decision block (803) evaluates false (803(*n*)), the Get Adaptive Limits method (at block 850) is executed followed by decision block (806). If block (806) evaluates true (806(*y*)), the adaptive status variable is set (808), the Adaptive K Factor method is executed and the method (760) is done (at block 813). Conversely, if decision block (806) evaluates false (806(*n*)) and block (807) evaluates true (807(*y*)), the adaptive status variable is set (811), the Adaptive K Factor method (880) is executed and the method (760) is done (at block 813). Conversely, if block (807) evaluates false (807 (*n*)), the adaptive status is set to be true (at block 810) and the method (760) is done (at block 813).

Figure 18B:
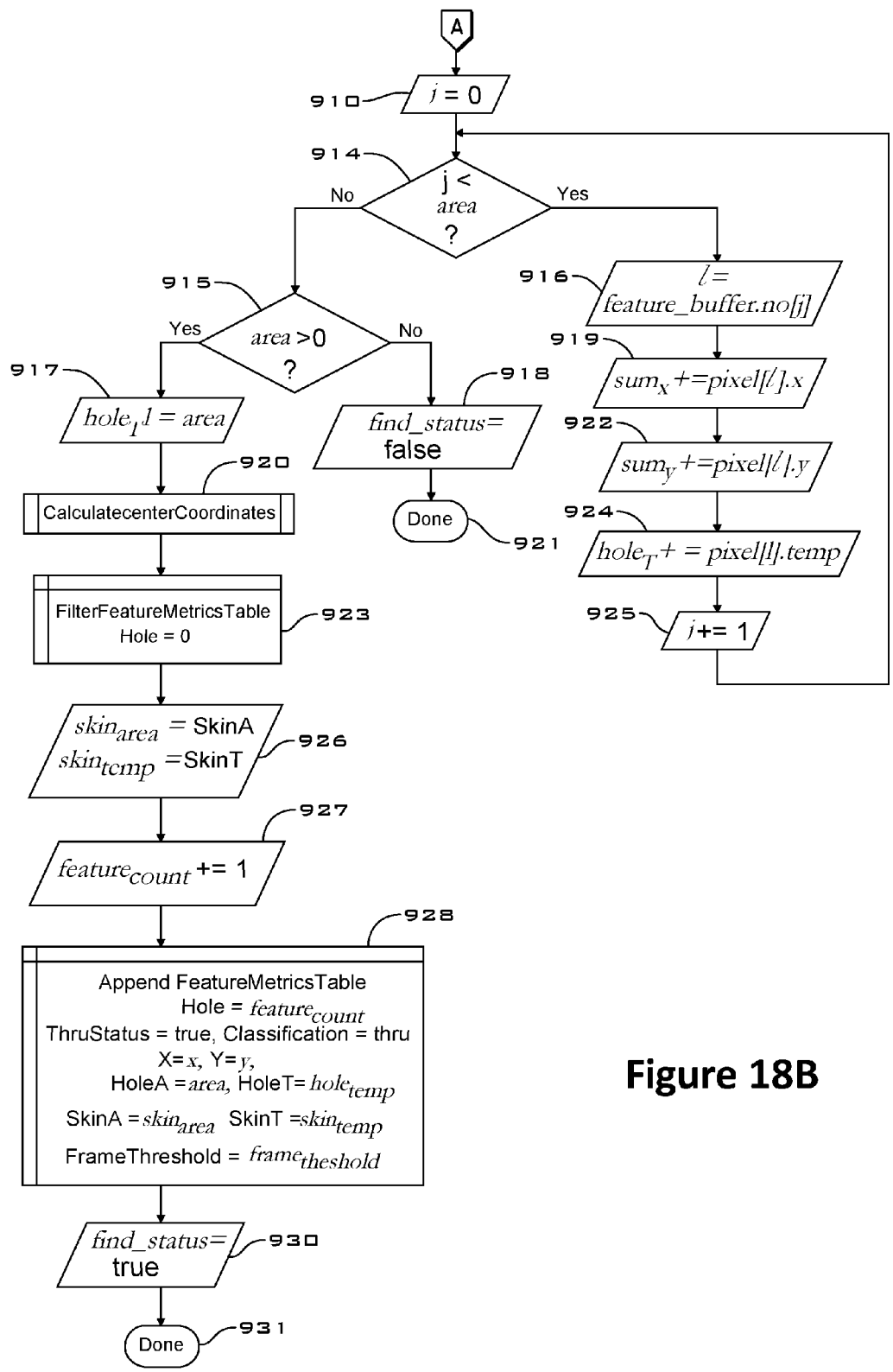
FIG. 18B is a continuation of the flow chart of FIG. 18A of the film cooling effect, feature and identification method for the embodiment of the FIG. 16 method.

In regards to FIGS. 18A and 18B, the Find Next Feature method (900) first initializes block (901) and decision block (902) evaluates false (902(*n*)), the Check Boundary Pixels method (903) is executed, the pixels counted is summed at block (905), and if the decision block (908) evaluates true (908(*y*)), the "l" variable is set to the frame buffer number array element (at block 911), the Check Boundary Pixels method (912) is executed, "j" is incremented (at block 913) and decision block 908 is repeated. If the decision block 902 evaluates true (902(*y*)), "i" is incremented by one (at block 904) and the decision block (906) evaluates false (906(*n*)), decision block (902) is repeated. Conversely, if decision block (906) evaluates true (906(*y*)), the find status is set (at block 907) and the Find Next Feature method (900) is done (at block 909). Conversely, if decision block 908 evaluates false (908(*n*)), "j" index is set to zero (at block 910) and if decision block (914) evaluates true (914(*y*)), "l" is set (at block 916), the sum x is summed (at block 919) the sum y is summed (at block 922), the hole is summed at block (924), "j" is incremented by one at block (925) and block (914) is repeated. Conversely, if decision block (914) evaluates false (914(*n*)) and decision block (915) evaluates false (915(*n*)), the find status is set (at block 918) and the Find Next Feature method (900) is done (at block 921). Conversely, if decision block (915) evaluates true (915(*y*)), the hole is set (at block 917), the Calculate Center Coordinates method is executed (at block 920), the feature metrics table is filtered (at block 923), the skin variables is set (at block 926), the feature count is incremented by one (at block 927), feature metrics table is appended (as set forth at block 928), the find status is set to true at block (930) and the Find Next Feature method (900) is done (at block 931).

In regards to FIG. 20, the Adaptive K Factor method (880), first if the decision block 881 evaluates true (881(*y*)), the features table is set (882), "i" is set to zero at block (884), and if decision block 887 evaluates true (887(*y*)), the features results table is appended (888), the missing hole symbol is displayed x, y (892), the features table is indexed (893), "i" is incremented by one (at block 894), and decision block (887) is repeated. Conversely, if decision block (887) evaluates false (887(*n*)), the adaptive status is set (889) and the Adaptive K Factor method (880) is done (at block 891). If decision block 881 evaluates false (881(*n*)) and decision block 883 evaluates true (883(*y*)), the adaptive weight is summed relative to Blob weight (at block 885), the adaptive status is set to false (at block 890) and the Adaptive K Factor method (880) is done (at block 891). Conversely, if the decision block (883) evaluates false (883(*n*)), the adaptive weight is summed relative to minor weight (at block 886), the adaptive status is set to false (at block 890) and the Adaptive K Factor method (880) is done (at block 891).

In regards to FIG. 21, the Classify Feature method (e.g., block 860), first if the classification is blocked or missing (1000(*y*)), the feature thru is set (1001) and the Classify Feature method (860) is done (1002). Conversely, if block (1000) evaluates false (1000(*n*)), and decision block 1003 evaluates true (1003(*y*)), the features results table is edited (1004), the partial symbol is displayed x, y (1005), the feature thru is set (1006) and the method (860) is done (1002). Conversely, if block (1003) evaluates false (1003(*n*)) and decision block (1007) evaluates true (1007(*y*)), the features result table is edited (1008), the blob symbol is displayed (1010), the feature thru is set (1012) and the Classify Feature method (860) is done (at block 1002). If block (1007) evaluates false (1007(*n*)), the features result table is edited (1009), the feature thru is set (1011) and the Classify Feature method (860) is done (at block 1002).

While the present invention has been illustrated by the description of various embodiments and while these embodiments have been described in considerable detail, there is no intention to restrict or in any way to limit the scope of the appended claims to such detail. Additional advantages and modifications will be readily appearing to those skilled in the art. For example, while the measurement processes described herein is directed to film cooling features fabricated in gas turbine blades, other applications can use this measurement process to inspect components such as nozzles, combustors, etc. For another example, while the measurement processes described herein uses a corrected mass rate of flow to quantify the flow rate of the cooling features, other solutions such as using a flow parameter to express the corrected mass rate of flow, can be used and yet the measurement results is within the spirit and scope of the claims made herein. Yet another example, the size and quantity of sonic nozzles used can be different than those described herein, dependent upon the component being inspected and still the measurement results remain within the spirit and scope of the claims herein made. Furthermore, those skilled in the art could use flow meters other than sonic nozzles to measure the mass rate of air flow and still its combination with a relative cooling effect remain within the spirit and scope of the claims herein made.

Therefore, the invention in its broadest aspects is not limited to the specific details shown and described herein. Consequently, departures may be made from the details described herein, without departing from the spirit and scope of the claims that follow.

What is claimed by this invention is:

1. An apparatus for measuring the film cooling effect generated by a film cooling hole that extends from a cavity within a component to an outer surface of the component, the apparatus comprising:
    an infrared measurement system;
    an airflow test system;
    a component holding fixture, common to both the infrared measurement and airflow test systems;
    a data acquisition system, common to both the infrared measurement and airflow test systems;
    a programmable controller, common to the infrared measurement, airflow test and data acquisition systems;
    a measurement data storage system, common to the programmable controller.

2. The apparatus of claim 1 wherein the infrared measurement system comprises a means to measure the relative individual film cooling effect generated by rapidly discharging a coolant to flow out of a film cooling hole and over a heated outer surface of the component.

3. The apparatus of claim 1 wherein the data acquisition system comprises an infrared camera, temperature measurement sensors, pressure measurement devices, voltage measurement devices, programmable voltage devices, digital control devices, digital signal devices, digital to analog devices, flow control devices, camera positioning device and safety devices.

4. The apparatus of claim 1 wherein the programmable control comprises electronic data processing units, memory devices, user interface devices, communication bus, and inspection program.

5. The apparatus of claim 1 wherein the data storage system comprises a networked relational database.

6. The apparatus of claim 1 wherein the airflow test machine comprises a means to control and measure the mass rate of air flowing into the cavity of the component and out of the plurality of film cooling holes.

7. The apparatus of claim 6 wherein said measurement of the mass rate of air accomplished using a critical flow Venturi nozzle mount in a removal, plug in module.

8. The apparatus of claim 1 wherein the component holding fixture comprises a suitably sized plenum, a flow conditioner, temperature and pressure measurement sensors, a means to hold a removable component adapter plate, a means to hold a component in contact with said plenum such that it does not leak, a means of directing either one of coolant and air.

9. The apparatus of claim 8 wherein the adapter plate holds the component stationary and a movable seal provides a conduit for a coolant to flow into the cavity and out the cooling holes fabricated in the component.

10. The apparatus of claim 9 wherein said coolant is helium.

11. An apparatus for measuring the film cooling effect generated by a film cooling hole that extends from a cavity within a component to an outer surface of the component, comprising:
    an infrared imaging system as a discrete apparatus;
    an airflow test system as a discrete apparatus;
    a common computing machine, that has the ability to process and store inspection data generated by the discrete infrared imaging and airflow test systems.

12. The apparatus of claim 11, wherein said infrared imaging system comprises:
    a component holding fixture;
    a data acquisition system; and
    a programmable controller.

13. The apparatus of claim 12, wherein said programmable controller comprises data processing units, memory devices, user interface devices, communication bus, and coded inspection program.

14. The apparatus of claim 11, wherein said airflow test system comprises:
    a component holding fixture;
    a data acquisition system; and
    a programmable controller.

15. The apparatus of claim 14, wherein said programmable controller comprises data processing units, memory devices, user interface devices, communication bus, and coded inspection program.

16. A method for measuring the individual film cooling effect generated by a film cooling hole that extends from a cavity within a component to an outer surface of the component, the method comprising the steps of:
    measure the mass rate of air flowing through a plurality of holes, each hole extending from a cavity;
    measure the relative cooling effect area generated by a hole that extends from a cavity;
    determine the film cooling effect generated by a film cooling hole that extends from a cavity within a component to an outer surface of the component, proportionate to the measurement of the mass rate of air flowing through the plurality of holes and the measurement of the film cooling effect area generated by an individual hole.

17. The method of claim 16 wherein said measurement of the relative cooling effect area of a hole that extends from a cavity, the method further comprising the steps of:
    a cooling effect is created on the outer surface of a component, by rapidly injecting a coolant and at the same time directing heat flux onto the outer surface of the component;
    measure an array of temperatures on the outer surface of a component using an infrared camera;
    analyze the array of temperatures to determine the size of the cooling effect;
    normalize the size of the cooling effect by correcting for the effects of dissimilar coolant pressure and imaging orientation.

18. The method of claim 16 wherein said measurement of the film cooling effect is a product of the portion of the normalized individual cooling effect area and the normalized mass rate of air.

19. The method of claim 17 wherein said measurement of the cooling effect area is accomplished by measurement of a characteristic infrared signature generated by a chilled and controlled gas that is discharged from the film cooling hole inspected relative to the hotter outer surface temperature of the component being inspected.

20. The method of claim 19 wherein said measurement of the infrared signature is identified by its significant temperature difference, the method comprising the steps of:
(a) a term adaptive$_{weight}$ is set to equal zero;
(b) compute a term k$_{factor}$ according to the following:

$$k_{factor}=k_A \times ROI_{min}^2 - k_B \times ROI_{min} + k_C + adpative_{weight}$$

(c) where constants k$_A$ and k$_B$ equals a value between 1 to 20 empirically determined, the constant k$_C$ equals a value between 0 to 20 empirically determined and the term ROI equals the minimum temperature found within the region of interest;
(d) compute a term ROI$_{threshold}$ according to the following:

$$ROI_{threshold}=\sqrt{k_{factor} \times ROI_{stdev} \times \log(ROI_{area})} + ROI_{min}$$

(e) where the term ROI$_{stdev}$ equals the standard deviation of the plurality of temperatures found within the region of interest and the term ROI$_{area}$ equals count of the plurality of temperatures found within the region of interest;
(f) comparing the first temperature found within the region of interest with the region of interest threshold;
(g) when said temperature is less than the threshold, it is identified as a significant pixel;
(h) iterating steps f and g for the plurality of temperatures;
(i) grouping the plurality of significant pixels into probable film cooling features using an eight cell test;
(j) computing the centroid for the plurality of probable film cooling features;
(k) comparing the coordinate of the centroid for the plurality of probable film cooling features with the expected center coordinate;
(l) when said centroid is within a programmed distance, the probable film cooling feature is identified as the infrared signature for the expected film cooling feature;
(m) compute the area of the infrared signature as its count of pixels;
(n) iterating steps j, k, l, and m for the plurality of probable film cooling features.

* * * * *

UNITED STATES PATENT AND TRADEMARK OFFICE
CERTIFICATE OF CORRECTION

PATENT NO.         : 9,274,009 B2
APPLICATION NO.    : 14/288484
DATED              : March 1, 2016
INVENTOR(S)        : Douglas E. Key It is certified that error appears in the above-identified patent and that said Letters Patent is hereby corrected as shown below:

In the Specification:

At column 1, line number 15, "088 is based upon and claims priority U.S. Provisional Patent" should read -- 088 is based upon and claims priority to expired U.S. Provisional Patent --

At column 3, line number 34, "machine further comprises of an upstream flow controller." should read -- machine further comprises an upstream flow controller. --

At column 3, line numbers 47-49, "sition method, first sets the upstream flow controller to a design specified flow condition. Then an assortment of pressures and temperatures is measured." should read -- sition method first sets the upstream flow controller to a design specified flow condition. Then an assortment of pressures and temperatures are measured. --

At column 3, line number 50, "The exemplary embodiment of the airflow test quantifica-" should read -- In the exemplary embodiment of the airflow test quantifica- --

At column 3, line number 56, "The exemplary embodiment of the relative individual cool-" should read -- In the exemplary embodiment of the relative individual cool- --

At column 5, line number 25, "generated by a film cooling features using the embodiments" should read -- generated by a film cooling feature using the embodiments --

At column 6, line number 59, "fixture (20) is both temperature (93) and pressure (92) sen-" should read -- fixture (20) are both temperature (93) and pressure (92) sen- --

At column 8, line number 8, "not affect the flow rate, and thus provides an accurate means" should read -- not affect the flow rate, and thus provide an accurate means --

At column 8, line number 33, "are stored in a network database (300) and is recalled by" should read -- are stored in a network database (300) and are recalled by --

At column 15, line number 4, "(300) for each position (521), shown in Fig. 13B, and is" should read -- (300) for each position (521), shown in Fig. 13B, and are --

Signed and Sealed this
Twelfth Day of July, 2016

Michelle K. Lee
*Director of the United States Patent and Trademark Office*

At column 15, line number 42, "ler. Both the array $I_f$ and descriptive statistics is stored in the" should read -- ler. Both the array $I_f$ and descriptive statistics are stored in the --

At column 15, line number 53, "by equation 16 where $b_0$ and $b_1$ is statistically determined" should read -- by equation 16 where $b_0$ and $b_1$ are statistically determined --

At column 16, line number 7, "820). The descriptive statistics for the $I_r$ array is computed at" should read -- 820). The descriptive statistics for the $I_r$ array are computed at --

At column 16, line number 63, "needed to for further processing. The control continues pro-" should read -- needed for further processing. The control continues pro- --

At column 17, line number 25, "(40), its area denoted $A_i$, and its $x_p$ and $y_p$ coordinate. This" should read -- (40), its area denoted $A_i$, and its $x_p$ and $y_p$ coordinates. This --

At column 17, line number 42, "$adaptive_{blob\_limit}$ is then computed as denoted by equations 19" should read -- $adaptive_{blob\_limit}$ are then computed as denoted by equations 19 --

At column 18, line number 1, "process using the new $ROI_{threshold}$ If p is less than the adap-" should read -- process using the new $ROI_{threshold}$. If p is less than the adap- --

At column 18, line number 39, "areas is determined. Using the value of the either mode or" should read -- areas is determined. Using the value of either the mode or --

At column 19, line number 37, "account. The $c_i$ computed as denoted by equation 26 or is" should read -- account. The $c_i$ is computed as denoted by equation 26 or is --

At column 19, approximately line number 45, in Equation 24, "$A_iO \rightarrow \rho_i = O$" should read -- $A_i = O \rightarrow \rho_i = O$ --

At column 22, line number 60, "art. For example, while the measurement processes described" should read -- art. For example, while the measurement process described --

At column 22, line number 64, "etc. For another example, while the measurement processes" should read -- etc. For another example, while the measurement process --

At column 23, line number 1, "flow, can be used and yet the measurement results is within" should read -- flow, can be used and yet the measurement results are within --

In the Claims:

At column 23, claim number 7, line numbers 53-55, "The apparatus of claim 6 wherein said measurement of the mass rate of air accomplished using a critical flow Venturi nozzle mount in a removal, plug in module." should read -- The apparatus of claim 6 wherein said measurement of the mass rate of air is accomplished using a critical flow Venturi nozzle mounted in a removable, plug in module. --

At column 25, claim number 20, approximately line number 7, "$k_{factor} = k_A \times ROI_{min}^2 - k_B \times$ At column 25, claim number 20, line numbers 9-13, "(c) where constants $k_A$ and $k_B$ equals a value between 1 to 20 empirically determined, the constant $k_C$ equals a value between 0 to 20 empirically determined and the term ROI equals the minimum temperature found within the region of interest;" should read -- where constants $k_A$ and $k_B$ equal a value between 1 to 20 empirically determined, the constant $k_C$ equals a value between 0 to 20 empirically determined and the term $ROI_{min}$ equals the minimum temperature found within the region of interest; --